United States Patent
Patel et al.

(10) Patent No.: US 12,257,257 B2
(45) Date of Patent: Mar. 25, 2025

(54) TESTOSTERONE DODECANOATE COMPOSITIONS AND METHODS

(71) Applicant: Lipocine, Inc., Salt Lake City, UT (US)

(72) Inventors: Mahesh V. Patel, Salt Lake City, UT (US); Kongnara Papangkorn, Salt Lake City, UT (US); Jonathan Ogle, Salt Lake City, UT (US); Nachiappan Chidambaram, Salt Lake City, UT (US); Benjamin J. Bruno, Salt Lake City, UT (US)

( * ) Notice: Subject to any disclaimer, the term of this patent is extended or adjusted under 35 U.S.C. 154(b) by 0 days.

(21) Appl. No.: 18/654,926

(22) Filed: May 3, 2024

(65) Prior Publication Data

US 2025/0032507 A1 Jan. 30, 2025

Related U.S. Application Data

(60) Provisional application No. 63/516,015, filed on Jul. 27, 2023.

(51) Int. Cl.
*A61K 31/568* (2006.01)
*A61K 9/00* (2006.01)

(52) U.S. Cl.
CPC .......... *A61K 31/568* (2013.01); *A61K 9/0053* (2013.01)

(58) Field of Classification Search
CPC ................................... A61K 31/568
See application file for complete search history.

(56) References Cited

U.S. PATENT DOCUMENTS

| | | | |
|---|---|---|---|
| 11,370,811 B1 * | 6/2022 | Kim | .......... C07J 9/005 |
| 11,672,807 B1 | 6/2023 | Chidambaram | |
| 11,931,367 B2 * | 3/2024 | Kim | ....... A61K 31/568 |
| 2005/0032762 A1 * | 2/2005 | Hubler | ........ A61K 47/44 |
| | | | 424/731 |
| 2019/0240235 A1 | 8/2019 | Nachaegari | |
| 2020/0390785 A1 | 12/2020 | Patel | |

* cited by examiner

*Primary Examiner* — Rei Tsang Shiao
(74) *Attorney, Agent, or Firm* — Michael R. Schramm

(57) ABSTRACT

Disclosed is a method and oral composition for treating a plurality of End stage diseases such as end-stage renal disease, chronic kidney disease, liver cirrhosis, chronic liver failure, end stage liver disease, Cancer, congestive Heart failure, pulmonary fibrosis, chronic obstructive pulmonary disease. In an embodiment of the invention, the composition comprises testosterone duodecanoate.

30 Claims, 2 Drawing Sheets

TESTOSTERONE DODECANOATE COMPOSITIONS AND METHODS

CROSS REFERENCE TO RELATED APPLICATIONS

This nonprovisional utility patent application claims the benefit under 35 USC § 119 (c) of U.S. provisional patent application No. 63/516,015 filed Jul. 27, 2023, which is expressly incorporated herein in its entirety by this reference. The following US patents and applications are also expressly incorporated herein in their entirety by this reference: 2020/0390785 to Patel et al. filed Aug. 25, 2020 and published Dec. 17, 2022, 2019/0240235 to Nachaegari et al. filed Nov. 5, 2018 and published Aug. 8, 2019, Ser. No. 17/573,592 to Bruno et al. filed Jan. 11, 2022, U.S. Pat. No. 11,370,811 to Kim et al. filed Nov. 20, 2020 and issued Jun. 28, 2022, and U.S. Pat. No. 11,672,807 to Chidambaram et al. filed December 23, 202 and issued Jun. 13, 2023.

FIELD OF THE INVENTION

The present disclosure relates to compositions, dosage forms and regimens, and methods of treating a subject in need of testosterone dodecanoate (TD). Accordingly, this disclosure involves the fields of chemistry, pharmaceutical sciences, medicine, and other health sciences.

BACKGROUND OF THE INVENTION

Testosterone dodecanoate (also known as testosterone laurate, testosterone duodecanoate, or TD), as shown is an ester of testosterone. Testosterone is the primary sex hormone and anabolic steroid in males. End stage disease (ESD) is a generalized term for any disorder that is likely to lead to death in a short time. ESD may include diseases such as end-stage renal disease (ESRD), chronic kidney disease (CKD), liver cirrhosis, chronic liver failure, end stage liver disease (ESLD), Cancer, congestive Heart failure (CHF), pulmonary fibrosis, chronic obstructive pulmonary disease (COPD). Endocrine disorder is commonly associated with an ESD. Insufficient levels of testosterone in men, especially with ESD, may lead to abnormalities including hypogonadism, sarcopenia, frailty, increased hospital admissions, poor quality of life, poor survival rates and increased mortality. Exogenous hormone therapy may be employed to treat men to counteract this endocrine dysfunction. Since testosterone oral bioavailability is low, the most widely used testosterone for testosterone therapy is in a form of testosterone ester.

Various methods of treatment and compositions therefor relating to various liver conditions are known in the art. Such methods and compositions are disclosed in the following list of US patent applications, all entitled "Liver Disease", and all of which are expressly incorporated herein in their entirety by this reference: 20200022991 entitled "Liver Disease" filed Aug. 28, 2019 and published Jan. 23, 2020, 20200155570 entitled "Liver Disease" filed Jul. 19, 2019 and published May 21, 2020, 2020038399 entitled "Liver Disease" filed Aug. 25, 2020 and published Dec. 10, 2020, 20200390785 entitled "Liver Disease" filed Aug. 25, 2020 and published Dec. 17, 2020, and 63/136,185 entitled "Method and Composition for Treating Non-Cirrhotic Nash" filed Jan. 11, 2021.

Cirrhosis is an ESD with liver transplant as the only cure (see Wikipedia entry for "Cirrhosis"). Typically, the cirrhosis is caused by several factors, such as alcohol, non-alcoholic fatty liver disease (NAFLD-see Wikipedia entry for "NAFLD"), drug abuse, chronic viral hepatitis, and autoimmune disease. Cirrhosis is a leading cause of death in the United States. The number of cases of liver disease in the United States and around the world is rapidly increasing, with the estimated prevalence of chronic liver disease in the United States believed to be between 6 and 7 million cases. Decompensated liver cirrhosis is estimated to affect more than 500,000 Americans, with men affected at twice the rate of women, and results in approximately 45,000 deaths every year. The only cure, liver transplant, has a high economic burden (~$878,500/transplant).

The hypothalamus-pituitary-gonadal axis is profoundly altered in advanced cirrhotic patients, leading to endocrine dysfunction. Men with chronic non-alcoholic liver disease had reduced levels of total and free testosterone and increased levels of sex hormone binding globulin (SHBG) compared with subjects with normal liver function. Subjects with cirrhosis have impaired hepatocellular function and reduced albumin synthesis due to dysregulated proteostasis. Cirrhosis is an inflamed disease state accompanied by increase in inflammation markers, leaky gut with increased gut permeability, increased portal hypertension, and compromised liver function with abnormal serum alkaline phosphatase (ALP) levels. Compromised bone health such as osteopenia and osteoporosis are also highly prevalent in individuals with liver cirrhosis.

Sarcopenia (loss of muscle mass/area) is observed in 60-80% of cirrhotic men, and frailty (a state of decreased physiological reserve) are associated with increased risk of hospitalization and hepatic decompensation events, a two-fold increase in waitlist mortality, and poor post-transplant outcomes (see Wikipedia entry for "Sarcopenia"). Moreover, myosteatosis (an excess of fat in muscle tissue-see Wiktionary entry for "myosteatosis") has been shown to correlate with low muscle mass, strength, and mobility, an increased MELD (Model for End-Stage Liver Disease) score (see Wikipedia entry for "Model for End-Stage Liver Disease"), worse median survival, and higher rates of mortality in patients with cirrhosis.

Hepatic encephalopathy (HE-see Wikipedia entry for "Hepatic encephalopathy") occurs frequently in patients with cirrhosis because of their end-stage liver disease. Approximately 30-50% of Cirrhotic individuals have overt HE (symptomatic). There are reported to be approximately 200,000 patients in the United States with overt HE. Clinically overt HE is significantly more prevalent in cirrhotic patients with muscle depletion, decreased muscle strength, or endocrine dysfunction. Overt hepatic encephalopathy (neurologic and neuropsychiatric abnormalities detected with bedside examination and bedside tests) occurs in approximately 30 to 40% of individuals with cirrhosis at some point during their illness. In recurrent HE, patients experience episodes of neurological dysfunction, which can last for several hours up to several days, followed by remission to baseline neurological function bouts within 6 months.

HE, a significant decompensation event, is a metabolically induced, potentially reversible, functional disturbance of the brain leading to "brain fog" associated with increased systemic ammonia levels. In patients with cirrhosis, myo/neuro toxic ammonia accumulates due to the compromised ability of the liver (primary organ) and muscles (secondary organ) to eliminate ammonia from systemic circulation. Furthermore, HE is a known risk factor for hospitalization, accidental trauma, and mortality. Additionally, anemia is a predictor of HE in cirrhotic liver transplant candidates. Potential risk factors for HE include Minimal HE and prior history of overt HE, sarcopenia, hyponatremia (see Wikipedia entry for "hyponatremia"), epilepsy (see Wikipedia entry for "epilepsy"), type 2 diabetes, higher creatinine and bilirubin levels and lower albumin levels.

Rifaximin, a semi-synthetic, non-systemic antibiotic, is currently approved for reduction of risk of overt HE recurrence and marketed as XIFAXAN® 550 mg tablets for oral administration with twice a day dosing. Reported mean rifaximin exposure (AUC) in patients with a history of HE with XIFAXAN® was approximately 12-fold higher than that observed in healthy subjects.

Currently, testosterone undecanoate (TU) is the only FDA approved testosterone ester that can be administered orally. Oral approved TU comprising products (e.g., JATENZO®, KYZATREX™, and TLANDO®) have a black box warning from FDA with respect to potential to increase blood pressure increases, per FDA approved prescribing information of JATENZO®, KYZATREX™, and TLANDO®, which may increase the risk of adverse cardiovascular events. The reported increase in blood pressure (BP) with the oral TU products ranged from a systolic BP of 1.7 mmHg to 5.4 mmHg based on ambulatory blood pressure monitoring (ABPM), whereas a diastolic mean BP increase ranged from 1.2 mmHg to 3.2 mmHg based on ABPM.

Moreover, these TU comprising oral approved products have the propensity to decrease high density lipoprotein (HDL) cholesterol levels in the patients who received TRT. A mean reduction in HDL-cholesterol of 6.9 mg/dL and 5.7 mg/dL was found in a patient who received JATENZO® and TLANDO®, respectively. For example, 29% of JATENZO®-treated subjects, 22% of TLANDO®-treated subjects had their HDL levels shifted from normal HDL-cholesterol at baseline to below the normal range after a period of testosterone treatment.

Furthermore, benign prostatic hyperplasia (BPH-see Wikipedia entry for "benign prostatic hyperplasia") and worsening of signs and symptoms of BPH are known in patients who received testosterone treatment. A clinical study showed that prostate specific antigen (PSA-see Wikipedia entry for "prostate specific antigen") increase (defined as a serum PSA concentration >4 ng/mL), prostate induration (see Wiktionary entry for "induration"), and prostate cancer were some of the most common adverse reactions reported, with occurrence rates of about 4.6%, 1.3%, and 1.3%, respectively in patients receiving an injectable TU composition. Prostate infection and prostate abnormality were also reported with TU injections-see the FDA approved label for AVEED®).

Therefore, the risks of cardiovascular disease, BPH, and prostate cancer are the main safety concerns for TRT. Lauric acid (LA-see Wikipedia entry for "lauric acid") is reportedly, associated with beneficial effects on the cardiovascular system due to its ability to increase HDL levels and to reduce the BP and heart rate in both normotensive and hypertensive rats. Moreover, LA has been shown to prevent the prostatic hyperplasia induced by testosterone in rats.

Reportedly, the use of current standard of care, rifaximin, to treat/manage HE in cirrhosis results in frequent adverse events (≥10%) including peripheral edema, nausea, dizziness, fatigue, and ascites in subjects with HE. Increase in livery injury marker, Alanine transferase (ALT) levels, has also been observed with oral rifaximin use. Moreover, there are concerns that long-term use of rifaximin and the potential for change in the gut flora and the development of resistance along with the potential for rifaximin to inhibit P-glycoprotein transporter. Given these limitations, there is an unmet need for an oral therapy that overcomes some of these limitations while treating/managing cirrhosis, an end stage disease.

We posit that oral testosterone therapy may provide a multimodal basis to treat end stage diseases such as cirrhosis. However, utility and approval of oral TU is currently limited to approval for hypogonadal subjects. TU has limitations due to its pharmacokinetics and pharmacodynamics including risks associated with cardiovascular and prostate health; therefore, rendering it suboptimal testosterone therapy for treatment/management of end stage disease such as liver cirrhosis.

There remains an unmet need in testosterone therapy (method and compositions) for a therapeutic option with a more favorable benefit to risk profile to treat/manage end stage disease with lower adverse event risk relative to other oral testosterone therapies with acceptable pharmacodynamic efficacy. The TD ester exbibits a unique physicochemical and biopharmaceutical properties relative other Testers.

We have surprisingly found that oral compositions and method of delivery of TD renders unique pharmacokinetic pharmacodynamic (PD) profiles relative to oral TU in treating/managing end stage disease such as cirrhosis independent of the gonadal status of the patient. TD's oral bioavailability is at least more than 20% different than other homologous esters of testosterone such as TU and testosterone tridecanoate (TT).

SUMMARY OF THE INVENTION

The present disclosure encompasses compositions and oral dosage forms and regimens comprising TD and related methods. The compositions and oral dosage forms may be formulated to include a therapeutically effective amount of TD and plurality of pharmaceutically acceptable additives. In one aspect, the pharmaceutically acceptable additive of the composition or dosage form may provide TD in an amount sufficient to treat an ESD such as ESRD, CKD, liver cirrhosis, chronic liver failure, ESLD, Cancer, CHF, pulmonary fibrosis, COPD, and specifically hypogonadism, sarcopenia, frailty, increased hospital admissions, poor quality of life, poor survival rates and increased mortality when orally administered to a subject. In another aspect, the composition or dosage form may include fast releasing or dissolving or solubilized forms of TD that may enhance, increase, or maximize bioavailability (e.g. $C_{max}$ and/or AUC) of TD when orally administered to a subject. For example, in one aspect, in vitro release, in vivo solubilization, and absorption of TD, when orally administered to a subject through compositions and methods of this invention, is increased. In another aspect, the absorption of TD, when orally administered to a subject through compositions and methods of this invention, is relatively increased as compared to a composition comprising an equivalent amount of a non-dodecanoate testosterone ester compositions when orally administered the subject.

In a first embodiment, the invention comprises a (preferably oral) method of administering the disclosed pharmaceutical composition that comprises or is prepared from TD (TDPC) to a subject, which as compared to a TDPC pre-administration state of the subject or a placebo administration to the subject, results in no deterioration in the subject of at least one of cardiovascular risk, cardiovascular health, prostate health, muscle health, CNS health, GI health, cell health, and median hospitalization duration, or an improvement in the subject of at least one of cardiovascular risk, cardiovascular health, prostate health, muscle health, CNS health, GI health, cell health, and median hospitalization duration.

The noted administration may also result in the subject at least one of a decrease in an SHBG level, an increase in an albumin level, a decrease in frailty, a decrease in sarcopenia, a decrease in myosteatosis, a decrease in fat mass, a decrease in systemic ammonia, a decrease in portal hypertension, a decrease in an abnormally high level of at least one of ALT, AST, GGT, and ALP, an increase in lean mass, an increase in free T, an increase in total T $C_{avg}$ by at least 100 ng/dL, an increase in a hematocrit level, an increase in a hemoglobin level, and a decrease in inflammation markers.

In the noted administration, the subject may have liver fibrosis and at least one of a MELD score of at least 12, at least one decompensation event, a BMI >20, an L3 muscle skeletal Index of <55 cm2/m2, a liver frailty index of >3, an ALT/AST ratio of about 1, an AST of >40 U/L, an abnormal ALT level, and an abnormal ALP level. L3 muscle skeletal Index is also referred to as "L3 SMI" is defined as a cross-sectional area of muscle tissue at the L3 level (see NCBI/NLM/NIH website for an article entitled, "Correlation between L3 skeletal muscle index and prognosis of patients with stage IV gastric cancer" also available at: https://www.ncbi.nlm.nih.gov/pmc/articles/PMC8576239/ #:~:text=L3%20SMI%20%3D %20 cross%2Dsectional%20area, status%20of%20patients%20with%20GC).

In the noted administration, the subject may have at least one of dysregulated proteostatis, an abnormally high SHBG level, and an abnormally low albumin level, and the subject may be in need of testosterone intervention based on a morning baseline testosterone level of at least one of <400 ng/dL, <350 ng/dL, <300 ng/dL, and <250 ng/dL.

In the noted administration, the cardiovascular risk may comprise risk of an adverse change in at least one of SBP, DBP, an HDL level, occurrence of ascites, a homocysteine level, and cardiac muscle mass or strength. A deterioration of cardiovascular health may comprise an adverse change in at least one of SBP, DBP, an HDL, occurrence of ascites, a homocysteine level, a cardiac reactive protein level, and cardiac muscle mass or strength, and an improvement of cardiovascular health may comprise a favorable change in the same. The deterioration of prostate health may comprise an adverse change in at least one of prostate gland size, prostate gland weight, and a BPH symptom, and an improvement of prostate health may comprises a favorable change in the same. The deterioration of muscle health may comprise an adverse change in at least one of muscle mass, muscle strength, muscle function, and muscle toxicity, and an improvement of muscle health may comprise a favorable change in the same. A deterioration of CNS health may comprise an adverse change in at least one of depression, seizure occurrence, cognition, risk of HE occurrence, risk of overt HE recurrence, breakthrough HE episodes, HE related hospitalizations, duration of time to onset of an episode of overt HE, HE recurrence reversal, occurrence of asterixis, mental status, intellectual function, psychometric test results, and neurophysiologic test results, and an improvement of CNS health may comprise a favorable change in the same. A deterioration of GI health may comprise an adverse change in at least one of diarrhea, microbial infection, *Clostridium difficile* infection, advanced liver disease, chronic liver disease, liver cirrhosis, chronic liver failure, quantity of liver injury markers, end-stage liver disease, hepatic fibrosis, hepatic inflammation, hepatic steatosis, NASH (also referred to as MASH—see Wikipedia entry for "Metabolic dysfunction-associated steatotic liver disease"), NAFLD, pre-liver transplant condition, post-liver transplant condition, PSC, and PBC, and an improvement of GI health may comprise a favorable change in the same.

In the noted administration, the adverse change in SBP may comprise an increase of SBP of at least 1.7 mmHg, and a favorable change in SBP may comprise a decrease of SBP of at least 1 mmHg.

In the noted administration, the condition may comprise at least one of carcinoma, sarcoma, melanoma, lymphoma, leukemia, end-stage liver disease, advanced liver disease, chronic liver disease, end-stage lung disease, chronic kidney disease, end-stage kidney disease, end-stage musculoskeletal system disease, end-stage cardiovascular disease, end-stage blood disease, end-stage endocrine gland disease, end-stage gastrointestinal disease, end-stage skin disease, end-stage genital organ disease, end-stage central nervous system disease, hepatic fibrosis, hepatic inflammation, hepatic steatosis, HE, recurrence of overt HE, NASH, NAFLD, pre/post liver transplant, decompensated cirrhosis, PBC, PSC, ILD, pneumonia, IPF, muscle mass wasting, cachexia, sarcopenia, frailty, type 1 diabetes, type 2 diabetes, hyperglycemia, glucose intolerance, hypogonadism, hypogonadotropic hypogonadism, a metabolic syndrome, visceral adiposity, obesity, impaired wound healing, large waist, myosteatosis, cancer, CHF, pulmonary fibrosis, COPD, and hereditary angioedema.

In the noted administration, the pharmaceutical composition may comprise at least one additive which may comprise at least one lipophilic additive and/or at least one hydrophilic additive. The at least one lipophilic additive may comprise at least one of a surfactant and a non-surfactant, and the at least one hydrophilic additive may comprise at least one of a surfactant and a non-surfactant.

In the noted administration, the pharmaceutical composition may comprise at least one carrier which may comprise at least one of a lipophilic carrier and a hydrophilic carrier. The lipophilic carrier may comprise at least one of a lipophilic surfactant and a lipophilic additive, and the hydrophilic carrier may comprise at least one of a hydrophilic surfactant and a hydrophilic additive. The lipophilic carrier may comprise at least one of a fatty acid, a derivative of a fatty acid, a vegetable oil, a derivative of a vegetable oil, a monoglyceride, a diglyceride, a triglyceride, a derivative of a monoglyceride, a derivative of a diglyceride, a derivative of a triglyceride, a sterol, a phytosterol, a tocopherol, a tocopherol succinate, a tocopherol acetate and a fish oil, and wherein said hydrophilic carrier comprises at least one of a polyoxyethylene hydrogenated vegetable oil, a polyoxyethylene vegetable oil, a polyethylene glycol fatty acid ester, a polyethylene glycol fatty acid monoglyceride mixture, a polyethylene glycol fatty acid diglyceride mixture, a polysorbate, a polyethylene glycol derivative of tocopherol, an alcohol, and an alcohol derivative. The fatty acid may comprise at least one of an oleic acid, a lauric acid, a stearic acid, and a derivative thereof, and wherein said vegetable oil comprises at least one of a peppermint oil, a sesame oil, a borage oil, a castor oil, a maize oil, a cottonseed oil, and a derivative thereof, and wherein said derivative of monoglyceride comprises at least one of glyceryl monolinoleate, and sorbitan mono-fatty acid, and wherein said derivative of diglyceride comprises glyceryl palmitostearate, and wherein said polyoxyethylene hydrogenated vegetable oil comprises PEG hydrogenated castor oil, and wherein said alcohol comprises at least one of ethyl alcohol and benzyl alcohol, and wherein said alcohol derivative comprises benzyl benzoate.

In the noted administration, the pharmaceutical composition may comprise at least one of a tablet, a capsule, a caplet, a gelcap, a suspension, a solution, a drink, a gel, a syrup, a dispersion, an emulsion, a sprinkle, a lozenge, a microemulsion, a nanocmulsion, an elixir, a paste, a powder, and a granule.

In the noted administration, the administration may include a dosing regimen that may comprise at least one of a QD regimen and a BID regimen. The dosing regimen may comprise at least one of a titration regimen and a non-titration regimen. The administration may comprise a total daily dose of TD of at least one of about 200 mg to about 1,000 mg, about 350 mg to about 850 mg, and about 500 mg to about 700 mg. The TDPC may have a dosage form comprising a single unit dosage form, a two unit dosage form, a three unit dosage for, and a four unit dosage form.

In the noted administration, the pharmaceutical composition may comprise at least one of an adsorbing agent, anti-adherents, anticoagulants, antifoaming agents, antioxidants, anti-caking colorants, anti-static agents, binders, bile acids, bufferants, bulking agents, chelating agents, coagulants, colorants, co-solvent, opaquants, congealing agents, coolants, cryoprotectants, diluents, dehumidifying agents, desiccants, desensitizers, disintegrants, dispersing agents, enzyme inhibitors, glidants, fillers, hydrating agent, super disintegrants, gums, mucilages, hydrogen bonding agents, enzymes, flavorants, humectants, humidifying agents, lubricant oils, ion-exchange resins, lubricants, plasticizers, pH modifying agents, preservatives, solidifying agent (solidifier), solvents, solubilizers, spreading agent sweeteners, stabilizers, surface area enhancing agents, suspending agent, thickeners, viscosity increasing agents, waxes and mixtures thereof. Anti-adherents (anti-sticking agents, glidants, flow promoters, lubricants) include, by way of non-limiting example, talc, magnesium stearate, fumed silica (Carbosil, Acrosil), micronized silica (Syloid No FP 244, Grace U.S.A.), polyethylene glycols, surfactants, waxes, stearic acid, stearic acid salts, stearic acid derivatives, starch, hydrogenated vegetable oils, sodium benzoate, sodium acetate, leucine, PEG-4000 and magnesium lauryl sulfate. Antioxidants include, by way of non-limiting example, BHT, BHA, gallic acid, propyl gallate, ascorbic acid, ascorbyl palmitate, 4-hydroxymethyl-2,6-di-tert-butyl phenol, and tocopherol. Binders (adhesives), i.e., agents that impart cohesive properties to powdered materials through particle-particle bonding, include, by way of non-limiting example, matrix binders (dry starch, dry sugars), film binders (PVP, starch paste, celluloses, bentonite, sucrose), and chemical binders (polymeric cellulose derivatives, such as carboxy methyl cellulose, HPC and HPNC, sugar syrups; corn syrup; water soluble polysaccharides such as acacia, tragacanth, guar and alginates; gelatin, gelatin hydrolysate; agar; sucrose; dextrose, and non-cellulosic binders, such as PVP, PEG, vinyl pyrrolidone copolymers, pregelatinized starch, sorbitol, and glucose). Buffering agents, include an acid and a base, wherein the acid is a pharmaceutically acceptable acid, such as hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, and the base is a pharmaceutically acceptable base, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a salt of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid. Chelating agents include, by way of non-limiting example, EDTA and EDTA salts Colorants or opaquants include, by way of non-limiting example, titanium dioxide, food dyes, lakes, natural vegetable colorants, iron oxides, silicates, sulfates, magnesium hydroxide and aluminum hydroxide. Diluents or fillers include, by way of non-limiting example, lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose. Disintegrants and super disintegrants include, by way of non-limiting example, croscarmellose sodium, starch, starch derivatives, clays, gums, cellulose, cellulose derivatives, alginates, crosslinked polyvinypyrrolidone, sodium starch glycolate and microcrystalline cellulose. Flavorants or desensitizers include, by way of non-limiting example, spray-dried flavors, essential oils and ethyl vanillin. Plasticizers include, by way of non-limiting example, polyethylene glycol, citrate esters (e.g., tricthyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl seccate. Preservatives include, by way of non-limiting example, ascorbic acid, boric acid, sorbic acid, benzoic acid, and salts thereof, parabens, phenols, benzyl alcohol, and quaternary ammonium compounds. Solvents include, by way of non-limiting example, alcohols, ketones, esters, chlorinated hydrocarbons and water. Sweeteners include, by way of non-limiting example, natural sweeteners such as maltose, sucrose, glucose, sorbitol, glycerin and dextrins, and artificial sweeteners, such as aspartame, saccharine and saccharine salts. Thickeners (viscosity modifiers, thickening agents) include, by way of non-limiting example, sugars, polyvinylpyrrolidone, cellulosics, polymers, high molecular weight polyethylene glycols (e.g., PEG 8000), and alginates. Additives also include, by way of non-limiting example, proteins (e.g., collagen, gelatin, Zein, gluten, mussel protein, lipoprotein); carbohydrates (e.g., alginates, carrageenan, cellulose derivatives, pectin, starch, chitosan): gums (e.g., xanthan gum, gum arabic); spermaceti; natural or synthetic waxes; carnuaba wax, fatty acids (e.g., stearic acid, hydroxystearic acid), fatty alcohols; sugars; shellacs, such as those based on sugars (e.g., lactose, sucrose, dextrose) or starches: polysaccharide-based shellacs (e.g., maltodextrin and maltodextrin derivatives, dextrates, cyclodextrin and cyclodextrin derivatives); cellulosic-based shellacs (e.g., microcrystalline cellulose, sodium carboxymethyl cellulose, hydroxypropylmethyl cellulose, ethyl cellulose, hydroxypropyl cellulose, cellulose acetate, cellulose nitrate, cellulose acetate butyrate, cellulose acetate trimellitate, carboxymethylethyl cellulose, hydroxypropylmethyl cellulose phthalate); inorganics, such as dicalcium phosphate, hydroxyapitite, tricalcium phosphate, talc and titania; polyols, such as mannitol, xylitol and sorbitol; polyethylene glycol esters; and polymers, such as alginates, poly (lactide coglycolide), gelatin, crosslinked gelatin, and agar-agar.

In a second embodiment, the invention comprises a (preferably oral) method of administering the disclosed pharmaceutical composition that comprises or is prepared from TD (TDPC) to a subject, which as compared to a substantially comparable administration of a pharmaceutical composition comprising at least one non-TD testosterone ester and being substantially TD-free (NDPC), results in less deterioration in said subject of at least one of a cardiovascular risk, cardiovascular health, prostate health, muscle health, CNS health, GI health, cell health, and median hospitalization duration, or greater improvement in said subject of at least one of a cardiovascular risk, cardiovascular health, prostate health, muscle health, CNS health, GI health, cell health, and median hospitalization duration.

The noted administration may also result in the subject at least one of a lower decrease in an HDL level relative to an HDL level resulting from the substantially comparable NDPC administration, an increase in bacterial inhibition activity, a decrease in an HbAle level of at least 0.2 units, a decrease in SBP, and a decrease in DBP.

In the noted administration, the subject may have liver fibrosis and at least one of a MELD score of at least 12, at least one decompensation event, a BMI >20, an L3 muscle skeletal Index of <55 cm2/m2, a liver frailty index of >3, an ALT/AST ratio of about 1, an AST of >40 U/L, an abnormal ALT level, and an abnormal ALP level.

In the noted administration, the subject may have at least one of dysregulated proteostatis, an abnormally high SHBG level, and an abnormally low albumin level, and the subject may be in need of testosterone intervention based on a morning baseline testosterone level of at least one of <400 ng/dL, <350 ng/dL, <300 ng/dL, and <250 ng/dL.

In the noted administration, the cardiovascular risk may comprise risk of an adverse change in at least one of SBP, DBP, an HDL level, occurrence of ascites, a homocysteine level, and cardiac muscle mass or strength. A deterioration of cardiovascular health may comprise an adverse change in at least one of SBP, DBP, an HDL, occurrence of ascites, a homocysteine level, a cardiac reactive protein level, and cardiac muscle mass or strength, and an improvement of cardiovascular health may comprise a favorable change in the same. The deterioration of prostate health may comprise an adverse change in at least one of prostate gland size, prostate gland weight, and a BPH symptom, and an improvement of prostate health may comprises a favorable change in the same. The deterioration of muscle health may comprise an adverse change in at least one of muscle mass, muscle strength, muscle function, and muscle toxicity, and an improvement of muscle health may comprise a favorable change in the same. A deterioration of CNS health may comprise an adverse change in at least one of depression, seizure occurrence, cognition, risk of HE occurrence, risk of overt HE recurrence, breakthrough HE episodes, HE related hospitalizations, duration of time to onset of an episode of overt HE, HE recurrence reversal, occurrence of asterixis, mental status, intellectual function, psychometric test results, and neurophysiologic test results, and an improvement of CNS health may comprise a favorable change in the same. A deterioration of GI health may comprise an adverse change in at least one of diarrhea, microbial infection, *Clostridium difficile* infection, advanced liver disease, chronic liver disease, liver cirrhosis, chronic liver failure, quantity of liver injury markers, end-stage liver disease, hepatic fibrosis, hepatic inflammation, hepatic steatosis, NASH, NAFLD, pre-liver transplant condition, post-liver transplant condition, PSC, and PBC, and an improvement of GI health may comprise a favorable change in the same.

In the noted administration, the adverse change in SBP may comprise an increase of SBP of at least 1.7 mmHg, and a favorable change in SBP may comprise a decrease of SBP of at least 1 mmHg.

In the noted administration, the condition may comprise at least one of carcinoma, sarcoma, melanoma, lymphoma, leukemia, end-stage liver disease, advanced liver disease, chronic liver disease, end-stage lung disease, chronic kidney disease, end-stage kidney disease, end-stage musculoskeletal system disease, end-stage cardiovascular disease, end-stage blood disease, end-stage endocrine gland disease, end-stage gastrointestinal disease, end-stage skin disease, end-stage genital organ disease, end-stage central nervous system disease, hepatic fibrosis, hepatic inflammation, hepatic steatosis, HE, recurrence of overt HE, NASH, NAFLD, pre/post liver transplant, decompensated cirrhosis, PBC, PSC, ILD, pneumonia, IPF, muscle mass wasting, cachexia, sarcopenia, frailty, type 1 diabetes, type 2 diabetes, hyperglycemia, glucose intolerance, hypogonadism, hypogonadotropic hypogonadism, a metabolic syndrome, visceral adiposity, obesity, impaired wound healing, large waist, myosteatosis, cancer, CHF, pulmonary fibrosis, COPD, and hereditary angioedema.

In the noted administration, the pharmaceutical composition may comprise at least one additive which may comprise a lipophilic additive or a hydrophilic additive. The lipophilic additive may comprise at least one of a surfactant and a non-surfactant, and the hydrophilic additive may comprise at least one of a surfactant and a non-surfactant.

In the noted administration, the pharmaceutical composition may comprise at least one carrier which may comprise at least one of a lipophilic carrier and a hydrophilic carrier. The lipophilic carrier may comprise at least one of a lipophilic surfactant and a lipophilic additive, and the hydrophilic carrier may comprise at least one of a hydrophilic surfactant and a hydrophilic additive. The lipophilic carrier may comprise at least one of a fatty acid, a derivative of a fatty acid, a vegetable oil, a derivative of a vegetable oil, a monoglyceride, a diglyceride, a triglyceride, a derivative of a monoglyceride, a derivative of a diglyceride, a derivative of a triglyceride, a sterol, a phytosterol, a tocopherol, a tocopherol succinate, a tocopherol acetate and a fish oil, and wherein said hydrophilic carrier comprises at least one of a polyoxyethylene hydrogenated vegetable oil, a polyoxyethylene vegetable oil, a polyethylene glycol fatty acid ester, a polyethylene glycol fatty acid monoglyceride mixture, a polyethylene glycol fatty acid diglyceride mixture, a polysorbate, a polyethylene glycol derivative of tocopherol, an alcohol, and an alcohol derivative. The fatty acid may comprise at least one of an oleic acid, a lauric acid, a stearic acid, and a derivative thereof, and wherein said vegetable oil comprises at least one of a peppermint oil, a sesame oil, a borage oil, a castor oil, a maize oil, a cottonseed oil, and a derivative thereof, and wherein said derivative of monoglyceride comprises at least one of glyceryl monolinoleate, and sorbitan mono-fatty acid, and wherein said derivative of diglyceride comprises glyceryl palmitostearate, and wherein said polyoxyethylene hydrogenated vegetable oil comprises PEG hydrogenated castor oil, and wherein said alcohol comprises at least one of ethyl alcohol and benzyl alcohol, and wherein said alcohol derivative comprises benzyl benzoate.

In the noted administration, the pharmaceutical composition may comprise at least one of a tablet, a capsule, a caplet, a gelcap, a suspension, a solution, a drink, a gel, a syrup, a dispersion, an emulsion, a sprinkle, a lozenge, a microemulsion, a nanoemulsion, an elixir, a paste, a powder, and a granule.

In the noted administration, the administration may include a dosing regimen that may comprise at least one of a QD regimen and a BID regimen. The dosing regimen may comprise at least one of a titration regimen and a non-titration regimen. The administration may comprise a total daily dose of TD of at least one of about 200 mg to about 1,000 mg, about 350 mg to about 850 mg, and about 500 mg to about 700 mg. The TDPC may have a dosage form comprising a single unit dosage form, a two unit dosage form, a three unit dosage for, and a four unit dosage form.

In a third embodiment, the invention comprises a (preferably oral) method of treating a condition in a subject comprising administering a TDPC to the subject, wherein the TDPC comprises or is prepared from at least one lipophilic additive, said at least one lipophilic additive comprising at least one of a fatty acid, a fatty acid derivative, and a combination thereof, and wherein in comparison to at least one of a TDPC pre-administration state of the subject and a placebo administration, the administration results in no deterioration in the subject of at least one of cardiovascular risk, cardiovascular health, prostate health, muscle health, CNS health, GI health, cell health, and median hospitalization duration, or an improvement in the subject of at least one of cardiovascular risk, cardiovascular health, prostate health, muscle health, CNS health, GI health, cell health, and median hospitalization duration.

The noted administration may also result in the subject at least one of a decrease in an SHBG level, an increase in an albumin level, a decrease in frailty, a decrease in sarcopenia, a decrease in myosteatosis, a decrease in fat mass, a decrease in systemic ammonia, a decrease in portal hypertension, a decrease in an abnormally high level of at least one of ALT, AST, GGT, and ALP, an increase in lean mass, an increase in free T, an increase in total T Cave by at least 100 ng/dL, an increase in a hematocrit level, an increase in a hemoglobin level, and a decrease in inflammation markers.

In the noted administration, the pharmaceutical composition may comprise at least one of an oleic acid or a derivative thereof, a lauric acid or a derivative thereof, a stearic acid or a derivative thereof, and a combination thereof.

In the noted administration, the TDPC comprises a w/w ratio of TD to lipophilic additive of at least one of a minimum of about 0.38, about 0.52, and about 0.60. In the noted administration, the TDPC comprises a w/w ratio of TD to hydrophilic additive of at least one of a minimum of about 4.0, about 5.4, and about 6.5.

In the noted administration, the subject may have liver fibrosis and at least one of a MELD score of at least 12, at least one decompensation event, a BMI >20, an L3 muscle skeletal Index of <55 cm2/m2, a liver frailty index of >3, an ALT/AST ratio of about 1, an AST of >40 U/L, an abnormal ALT level, and an abnormal ALP level.

In the noted administration, the subject may have at least one of dysregulated proteostatis, an abnormally high SHBG level, an abnormally low albumin level, and the subject may be in need of testosterone intervention based on a morning baseline testosterone level of at least one of <400 ng/dL, <350 ng/dL, <300 ng/dL, and <250 ng/dL.

In the noted administration, the cardiovascular risk may comprise risk of an adverse change in at least one of SBP, DBP, an HDL level, occurrence of ascites, a homocysteine level, and cardiac muscle mass or strength. A deterioration of cardiovascular health may comprise an adverse change in at least one of SBP, DBP, an HDL, occurrence of ascites, a homocysteine level, a cardiac reactive protein level, and cardiac muscle mass or strength, and an improvement of cardiovascular health may comprise a favorable change in the same. The deterioration of prostate health may comprise an adverse change in at least one of prostate gland size, prostate gland weight, and a BPH symptom, and an improvement of prostate health may comprises a favorable change in the same. The deterioration of muscle health may comprise an adverse change in at least one of muscle mass, muscle strength, muscle function, and muscle toxicity, and an improvement of muscle health may comprise a favorable change in the same. A deterioration of CNS health may comprise an adverse change in at least one of depression, seizure occurrence, cognition, risk of HE occurrence, risk of overt HE recurrence, breakthrough HE episodes, HE related hospitalizations, duration of time to onset of an episode of overt HE, HE recurrence reversal, occurrence of asterixis, mental status, intellectual function, psychometric test results, and neurophysiologic test results, and an improvement of CNS health may comprise a favorable change in the same. A deterioration of GI health may comprise an adverse change in at least one of diarrhea, microbial infection, *Clostridium difficile* infection, advanced liver disease, chronic liver disease, liver cirrhosis, chronic liver failure, quantity of liver injury markers, end-stage liver disease, hepatic fibrosis, hepatic inflammation, hepatic steatosis, NASH, NAFLD, pre-liver transplant condition, post-liver transplant condition, PSC, and PBC, and an improvement of GI health may comprise a favorable change in the same.

In the noted administration, the adverse change in SBP may comprise an increase of SBP of at least 1.7 mmHg, and a favorable change in SBP may comprise a decrease of SBP of at least 1 mmHg.

In the noted administration, the condition may comprise at least one of carcinoma, sarcoma, melanoma, lymphoma, leukemia, end-stage liver disease, advanced liver disease, chronic liver disease, end-stage lung disease, chronic kidney disease, end-stage kidney disease, end-stage musculoskeletal system disease, end-stage cardiovascular disease, end-stage blood disease, end-stage endocrine gland disease, end-stage gastrointestinal disease, end-stage skin disease, end-stage genital organ disease, end-stage central nervous system disease, hepatic fibrosis, hepatic inflammation, hepatic steatosis, HE, recurrence of overt HE, NASH, NAFLD, pre/post liver transplant, decompensated cirrhosis, PBC, PSC, ILD, pneumonia, IPF, muscle mass wasting, cachexia, sarcopenia, frailty, type 1 diabetes, type 2 diabetes, hyperglycemia, glucose intolerance, hypogonadism, hypogonadotropic hypogonadism, a metabolic syndrome, visceral adiposity, obesity, impaired wound healing, large waist, myosteatosis, cancer, CHF, pulmonary fibrosis, COPD, and hereditary angioedema.

In the noted administration, the pharmaceutical composition may comprise at least one additive which may comprise a lipophilic additive or a hydrophilic additive. The lipophilic additive may comprise at least one of a surfactant and a non-surfactant, and the hydrophilic additive may comprise at least one of a surfactant and a non-surfactant.

In the noted administration, the pharmaceutical composition may comprise at least one carrier which may comprise at least one of a lipophilic carrier and a hydrophilic carrier. The lipophilic carrier may comprise at least one of a lipophilic surfactant and a lipophilic additive, and the hydrophilic carrier may comprise at least one of a hydrophilic surfactant and a hydrophilic additive. The lipophilic carrier may comprise at least one of a fatty acid, a derivative of a fatty acid, a vegetable oil, a derivative of a vegetable oil, a monoglyceride, a diglyceride, a triglyceride, a derivative of a monoglyceride, a derivative of a diglyceride, a derivative of a triglyceride, a sterol, a phytosterol, a tocopherol, a tocopherol succinate, a tocopherol acetate and a fish oil, and wherein said hydrophilic carrier comprises at least one of a polyoxyethylene hydrogenated vegetable oil, a polyoxyethylene vegetable oil, a polyethylene glycol fatty acid ester, a polyethylene glycol fatty acid monoglyceride mixture, a polyethylene glycol fatty acid diglyceride mixture, a polysorbate, a polyethylene glycol derivative of tocopherol, an alcohol, and an alcohol derivative. The fatty acid may comprise at least one of an oleic acid, a lauric acid, a stearic acid, and a derivative thereof, and wherein said vegetable oil comprises at least one of a peppermint oil, a sesame oil, a borage oil, a castor oil, a maize oil, a cottonseed oil, and a derivative thereof, and wherein said derivative of monoglyceride comprises at least one of glyceryl monolinoleate, and sorbitan mono-fatty acid, and wherein said derivative of diglyceride comprises glyceryl palmitostearate, and wherein said polyoxyethylene hydrogenated vegetable oil comprises PEG hydrogenated castor oil, and wherein said alcohol comprises at least one of ethyl alcohol and benzyl alcohol, and wherein said alcohol derivative comprises benzyl benzoate.

In the noted administration, the pharmaceutical composition may comprise at least one of a tablet, a capsule, a caplet, a gelcap, a suspension, a solution, a drink, a gel, a syrup, a dispersion, an emulsion, a sprinkle, a lozenge, a microemulsion, a nanoemulsion, an elixir, a paste, a powder, and a granule.

In the noted administration, the administration may include a dosing regimen that may comprise at least one of a QD regimen and a BID regimen. The dosing regimen may comprise at least one of a titration regimen and a non-titration regimen. The administration may comprise a total daily dose of TD of at least one of about 200 mg to about 1,000 mg, about 350 mg to about 850 mg, and about 500 mg to about 700 mg. The TDPC may have a dosage form comprising a single unit dosage form, a two unit dosage form, a three unit dosage for, and a four unit dosage form.

In a fourth embodiment, the invention comprises a (preferably oral) method of treating a condition in a subject comprising administering a TDPC to the subject, wherein the TDPC comprises or is prepared from at least one lipophilic additive, said at least one lipophilic additive comprising at least one of a fatty acid, a fatty acid derivative, and a combination thereof, and wherein in comparison to a substantially comparable administration of a pharmaceutical composition comprising at least one non-TD testosterone ester and being substantially TD-free (NDPC), the administration results in less deterioration in said subject of at least one of a cardiovascular risk, cardiovascular health, prostate health, muscle health, CNS health, GI health, cell health, and median hospitalization duration, and greater improvement in said subject of at least one of a cardiovascular risk, cardiovascular health, prostate health, muscle health, CNS health, GI health, cell health, and median hospitalization duration.

The noted administration may also result in the subject at least one of a lower decrease in an HDL level relative to an HDL level resulting from the substantially comparable NDPC administration, an increase in bacterial inhibition activity, a decrease in an HbA1c level of at least 0.2 units, a decrease in SBP, and a decrease in DBP.

In the noted administration, the pharmaceutical composition may comprise at least one of an oleic acid or a derivative thereof, a lauric acid or a derivative thereof, a stearic acid or a derivative thereof, and a combination thereof.

In the noted administration, the TDPC comprises a w/w ratio of TD to lipophilic additive of at least one of a minimum of about 0.38, about 0.52, and about 0.60. In the noted administration, the TDPC comprises a w/w ratio of TD to hydrophilic additive of at least one of a minimum of about 4.0, about 5.4, and about 6.5.

In the noted administration, the subject may have liver fibrosis and at least one of a MELD score of at least 12, at least one decompensation event, a BMI >20, an L3 muscle skeletal Index of <55 cm2/m2, a liver frailty index of >3, an ALT/AST ratio of about 1, an AST of >40 U/L, an abnormal ALT level, and an abnormal ALP level.

In the noted administration, the subject may have at least one of dysregulated proteostatis, an abnormally high SHBG level, and an abnormally low albumin level, and the subject may be in need of testosterone intervention based on a morning baseline testosterone level of at least one of <400 ng/dL, <350 ng/dL, <300 ng/dL, and <250 ng/dL.

In the noted administration, the cardiovascular risk may comprise risk of an adverse change in at least one of SBP, DBP, an HDL level, occurrence of ascites, a homocysteine level, and cardiac muscle mass or strength. A deterioration of cardiovascular health may comprise an adverse change in at least one of SBP, DBP, an HDL, occurrence of ascites, a homocysteine level, a cardiac reactive protein level, and cardiac muscle mass or strength, and an improvement of cardiovascular health may comprise a favorable change in the same. The deterioration of prostate health may comprise an adverse change in at least one of prostate gland size, prostate gland weight, and a BPH symptom, and an improvement of prostate health may comprises a favorable change in the same. The deterioration of muscle health may comprise an adverse change in at least one of muscle mass, muscle strength, muscle function, and muscle toxicity, and an improvement of muscle health may comprise a favorable change in the same. A deterioration of CNS health may comprise an adverse change in at least one of depression, seizure occurrence, cognition, risk of HE occurrence, risk of overt HE recurrence, breakthrough HE episodes, HE related hospitalizations, duration of time to onset of an episode of overt HE, HE recurrence reversal, occurrence of asterixis, mental status, intellectual function, psychometric test results, and neurophysiologic test results, and an improvement of CNS health may comprise a favorable change in the same. A deterioration of GI health may comprise an adverse change in at least one of diarrhea, microbial infection, *Clostridium difficile* infection, advanced liver disease, chronic liver disease, liver cirrhosis, chronic liver failure, quantity of liver injury markers, end-stage liver disease, hepatic fibrosis, hepatic inflammation, hepatic steatosis, NASH, NAFLD, pre-liver transplant condition, post-liver transplant condition, PSC, and PBC, and an improvement of GI health may comprise a favorable change in the same.

In the noted administration, the adverse change in SBP may comprise an increase of SBP of at least 3 mmHg, and a favorable change in SBP may comprise a decrease of SBP of at least 1 mmHg.

In the noted administration, the condition may comprise at least one of carcinoma, sarcoma, melanoma, lymphoma, leukemia, end-stage liver disease, advanced liver disease, chronic liver disease, end-stage lung disease, chronic kidney disease, end-stage kidney disease, end-stage musculoskeletal system disease, end-stage cardiovascular disease, end-stage blood disease, end-stage endocrine gland disease, end-stage gastrointestinal disease, end-stage skin disease, end-stage genital organ disease, end-stage central nervous system disease, hepatic fibrosis, hepatic inflammation, hepatic steatosis, HE, recurrence of overt HE, NASH, NAFLD, pre/post liver transplant, decompensated cirrhosis, PBC, PSC, ILD, pneumonia, IPF, muscle mass wasting, cachexia, sarcopenia, frailty, type 1 diabetes, type 2 diabetes, hyperglycemia, glucose intolerance, hypogonadism, hypogonadotropic hypogonadism, a metabolic syndrome, visceral adiposity, obesity, impaired wound healing, large waist, myosteatosis, cancer, CHF, pulmonary fibrosis, COPD, and hereditary angioedema.

In the noted administration, the pharmaceutical composition may comprise at least one additive which may comprise a lipophilic additive or a hydrophilic additive. The lipophilic additive may comprise at least one of a surfactant and a non-surfactant, and the hydrophilic additive may comprise at least one of a surfactant and a non-surfactant.

In the noted administration, the pharmaceutical composition may comprise at least one carrier which may comprise at least one of a lipophilic carrier and a hydrophilic carrier. The lipophilic carrier may comprise at least one of a lipophilic surfactant and a lipophilic additive, and the hydrophilic carrier may comprise at least one of a hydrophilic surfactant and a hydrophilic additive. The lipophilic carrier may comprise at least one of a fatty acid, a derivative of a fatty acid, a vegetable oil, a derivative of a vegetable oil, a monoglyceride, a diglyceride, a triglyceride, a derivative of a monoglyceride, a derivative of a diglyceride, a derivative of a triglyceride, a sterol, a phytosterol, a tocopherol, a tocopherol succinate, a tocopherol acetate and a fish oil, and wherein said hydrophilic carrier comprises at least one of a polyoxyethylene hydrogenated vegetable oil, a polyoxyethylene vegetable oil, a polyethylene glycol fatty acid ester, a polyethylene glycol fatty acid monoglyceride mixture, a polyethylene glycol fatty acid diglyceride mixture, a polysorbate, a polyethylene glycol derivative of tocopherol, an alcohol, and an alcohol derivative. The fatty acid may comprise at least one of an oleic acid, a lauric acid, a stearic acid, and a derivative thereof, and wherein said vegetable oil comprises at least one of a peppermint oil, a sesame oil, a borage oil, a castor oil, a maize oil, a cottonseed oil, and a derivative thereof, and wherein said derivative of monoglyceride comprises at least one of glyceryl monolinoleate, and sorbitan mono-fatty acid, and wherein said derivative of diglyceride comprises glyceryl palmitostearate, and wherein said polyoxyethylene hydrogenated vegetable oil comprises PEG hydrogenated castor oil, and wherein said alcohol comprises at least one of ethyl alcohol and benzyl alcohol, and wherein said alcohol derivative comprises benzyl benzoate.

In the noted administration, the pharmaceutical composition may comprise at least one of a tablet, a capsule, a caplet, a gelcap, a suspension, a solution, a drink, a gel, a syrup, a dispersion, an emulsion, a sprinkle, a lozenge, a microemulsion, a nanoemulsion, an elixir, a paste, a powder, and a granule.

In the noted administration, the administration may include a dosing regimen that may comprise at least one of a QD regimen and a BID regimen. The dosing regimen may comprise at least one of a titration regimen and a non-titration regimen. The administration may comprise a total daily dose of TD of at least one of about 200 mg to about 1,000 mg, about 350 mg to about 850 mg, and about 500 mg to about 700 mg. The TDPC may have a dosage form comprising a single unit dosage form, a two unit dosage form, a three unit dosage for, and a four unit dosage form.

In a fifth embodiment, the invention comprises a (preferably oral) method of treating a condition in a subject comprising administering a TDPC to the subject, wherein the administration of the TDPC may enhance a subject's indicators used to monitor liver disease (e.g., L3-SMI). By way of example, administration of the TDPC may increase the subject's L3-SMI. By way of other examples, the administration of the TDPC may increase the subject's muscle area (e.g., muscle area monitored by the L3 region of a CT scan), decrease a subject's intramuscular adipose tissue (IMAT or myosteatosis) (e.g., IMAT monitored by the L3 region of a CT scan), increase muscle quality (increase in muscle area identified between 30 and 150 HU monitored by the L3 region of a CT scan). By way of another example, administration of the TDPC may resolve a subject's anemic status. By way of another example, administration of the TDPC may increase the subject's perceived quality of life on drug (e.g., the subject may report feeling better using PGI-C response). By way of still another example, the administration of the TDPC may decrease the subject's decompensation events (e.g., ascites, hepatic encephalopathy, varices, or spontaneous bacterial peritonitis), increase the amount of time between subject's decompensation event recurrence, decrease in number of days per hospitalization, decrease in total number of hospitalization days, or decrease a subject's Stroop test time (see the Wikipedia website for "Stroop effect" available at: https://en.wikipedia.org/wiki/Stroop_effect).

By way of example, the TDPC, when administered to 15 randomized subjects and compared to a placebo administration administered to 10 subjects has shown an increase in L3-SMI to the TDPC administered subjects relative to baseline L3-SMI and when compared to the placebo subjects. These trends are maintained similarly in at least the previously described endpoints including increase in subject muscle area, muscle quality, perceived quality of life, and decrease in IMAT, decompensation events, and Stroop test time.

The exemplary proceeding endpoint calculations are performed with LS Mean (SE) calculated from an ANOVA considering baseline and treatment arm relative to change from baseline (L3-SMI), considering treatment arm relative to score (PGI-C), or considering the binomial distribution of event statistics (hepatic encephalopathy) which does not have a baseline characterization and considers treatment arm relative to score. Increase in L3-SMI from baseline was shown to be 2.64 (0.84) for TDPC administered treatment after a given time (e.g., 12 weeks) to be statistically distinguishable from baseline. Additionally, increase in L3-SMI from baseline was shown to be 3.62 (0.93) for TDPC administered treatment after a given time (e.g., 24 weeks) to be statistically distinguishable from baseline, and was further statistically distinguishable from the placebo administered subjects with L3-SMI-0.74 (1.14). PGI-C scores for TDPC administered treatment were 3.00 (0.25) and were determined to be statistically distinguishable from placebo administered subjects scoring 3.85 (0.26). Hepatic encephalopathy decompensation events were statistically fewer in the TDPC administered treatment (e.g., 2 events) when compared to the placebo administered subjects (e.g., 6 events). Furthermore, recurrence of decompensation events greater than grade 1 (e.g., HE) may also be delayed, with a mean recurrence of 115 for the TDPC administered treatment, and 39 days for the placebo administered subjects. These examples show significant unexpected benefits arising from the described TDPC. Other exemplary endpoints may be statistically significant, or the trend between TDPC and placebo suggests benefit.

The benefits of the TDPC administered treatment are further supported by the lack of clinical benefit that may be observed with lower dose administrations (e.g., 50 mg loading TDPC administered once daily for sub-chronic treatment). By way of example a lower dose TDPC administration may not enhance a subject's indicators used to monitor liver disease (e.g., L3-SMI). By way of example, administration of the lower dose TDPC may not increase the subject's L3-SMI. By way of other examples, the administration of a lower dose TDPC may not increase the subject's muscle area (e.g., muscle area monitored by the L3 region of a CT scan), not decrease a subject's intramuscular adipose tissue (IMAT) (e.g., IMAT monitored by the L3 region of a CT scan), not increase muscle quality (increase in muscle area identified between 30 and 150 HU monitored by the L3 region of a CT scan). By way of another example, administration of the TDPC may not resolve a subject's anemic status. By way of another example, administration of a lower dose TDPC may not increase the subject's perceived quality of life on drug (e.g., the subject may report feeling better using PGI-C response). By way of still another example, a lower dose administration of the TDPC may not decrease the subject's decompensation events (e.g., ascites, hepatic encephalopathy, varices, or spontaneous bacterial peritonitis), not increase the amount of time between subject's decompensation event recurrence, not decrease the number of days per hospitalization, not decrease in total number of hospitalization days, or not decrease a subject's Stroop test time.

The benefits of TDPC administered treatment including improvements in muscle area, muscle quality, fat area, PGI-C questionnaire score, and other benefits discussed above alone or in combination with the observed outcomes in exemplary lower dosage TDPC administrations, lead to and show beneficial clinical outcomes in sarcopenia and decompensation events from the exemplary TDPC administration.

In addition to the other embodiments disclosed herein, it is noted that in certain embodiments testosterone tridecanoate may be substituted for TD with commensurate adjustments to the respective dosing regimens (e.g., a total daily dose of 600 mg to 1500 mg, 300 mg to 750 mg, or 150 mg to 375 mg).

BRIEF DESCRIPTION OF THE DRAWINGS

Features and advantages of invention embodiments will be apparent from the detailed description which follows, taken in conjunction with the accompanying drawings, which together illustrate, by way of example, features of the disclosure; and, wherein.

DETAILED DESCRIPTION OF THE INVENTION

Figure 1:
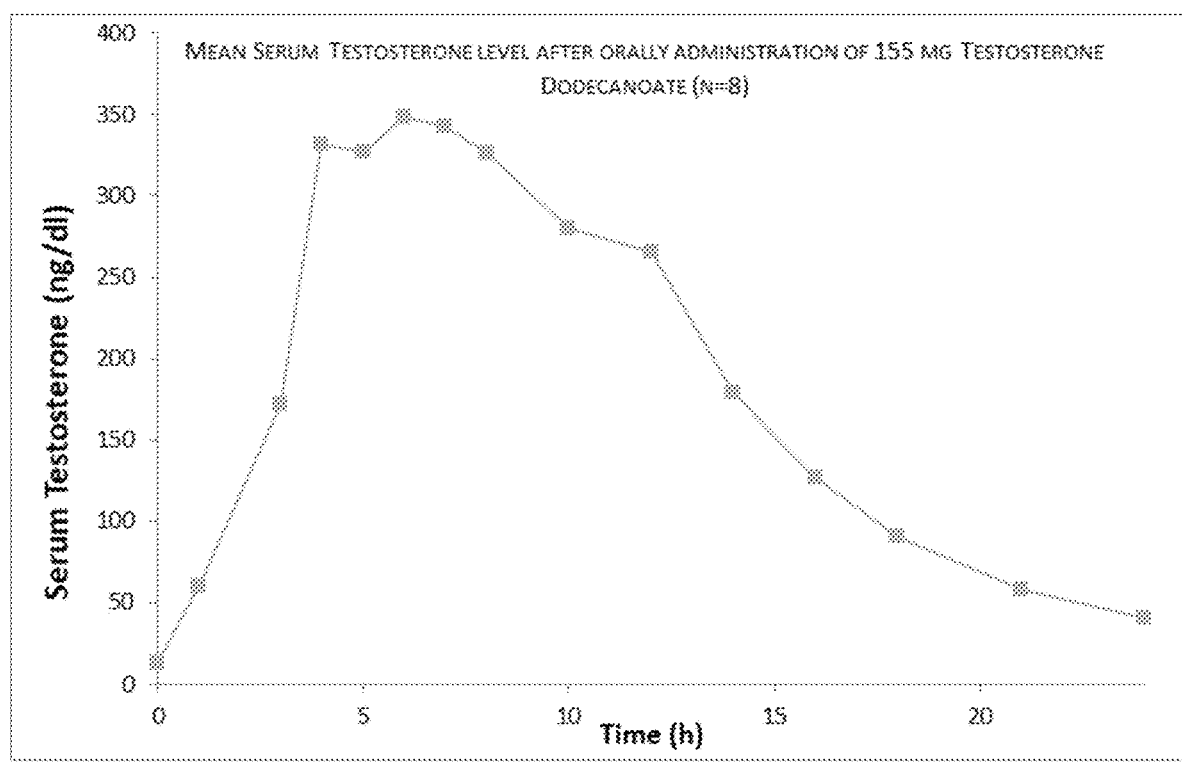
FIG. 1 is a plot of a pharmacokinetic profile of a mean serum testosterone level after orally administering 155 mg of TD.

Before invention embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting.

Furthermore, the described features, structures, or characteristics can be combined in any suitable manner in one or more embodiments. In the following description, numerous specific details are provided, such as examples of compositions, dosage forms, treatments, etc., to provide a thorough understanding of various invention embodiments. One skilled in the relevant art will recognize, however, that such detailed embodiments do not limit the overall inventive concepts articulated herein but are merely representative thereof.

Definitions

As used herein, the terms "treat," "treatment," or "treating" and the like refers to administration of a therapeutic agent to a subject who is either asymptomatic or symptomatic. In other words, "treat," "treatment," or "treating" can refer to the act of reducing or eliminating a condition (i.e., symptoms manifested), or it can refer to prophylactic treatment (i.e., administering to a subject not manifesting symptoms in order to prevent their occurrence). Such prophylactic treatment can also be referred to as prevention of the condition, preventative action, preventative measures, and the like.

As used herein, the terms "therapeutic agent," "active agent," and the like can be used interchangeably and refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical and medicinal arts. Further, when these terms are used, or when a particular active agent is specifically identified by name or category in this written description, it is understood that such recitation is intended to include express support for the active agent per se, as well as pharmaceutically acceptable salts, esters or compounds significantly related thereto, including without limitation, prodrugs, active metabolites, polymorphs, and the like. For example, recitation of the active agent allopregnanolone also includes express support for the active metabolites.

As used herein, the terms "formulation" and "composition" are used interchangeably and refer to a mixture of two or more compounds, elements, or molecules. In some aspects, the terms "formulation" and "composition" may be used to refer to a mixture of one or more active agents with an additive or other excipients. Furthermore, the term "dosage form" can include one or more formulation(s) or composition(s) provided in a format for administration to a subject. For example, an "oral dosage form" can be suitable for administration to a subject's mouth. A "topical dosage form" can be suitable for administration to a subject's skin by rubbing, etc.

As used herein, "pharmaceutically acceptable additive" or "additive" is used interchangeably and refer to a pharmaceutically acceptable agent or ingredient that can be combined with an active agent as part of a composition or dosage form. In some aspects, pharmaceutically acceptable additives can impact the form or behavior of an active agent. For example, in some aspects, a pharmaceutically acceptable additive can be capable of fully or partially dissolving or solubilizing an active agent (e.g., allopregnanolone) in a pharmaceutical composition or enabling a non-crystalline form of the active agent. In other aspects, a pharmaceutically acceptable additive can be formulated with an active agent (e.g., allopregnanolone) in a pharmaceutical composition comprising a crystalline form of the active agent. In one aspect, a composition, wherein the allopregnanolone comprises at least one form of substantially solubilized, partially solubilized, substantially non-solubilized, substantially crystalline, partially crystalline, substantially non-crystalline, amorphous, solid, a dispersion, and a eutectic mixture.

Further, in some aspects, the additives can impact or control the properties and performance of the composition or dosage form. For example, in some aspects, additives can impact or control the pharmacokinetic (PK) performance or profile (e.g., release rate and/or extent of release of the active agent) of the composition and/or the dosage form.

As used herein, a "semi-liquid" or "semi-solid" corresponds to a partially solubilized active agent and a "liquid" corresponds to a fully solubilized active agent at room temperature.

As used herein, a "subject" refers to a mammal that may benefit from the administration of a drug composition, dosage form or dosage regimen, or method disclosed herein. Examples of subjects include humans, and may also include other animals such as horses, pigs, cattle, dogs, cats, rabbits, and aquatic mammals. In one specific aspect, a subject is a human. In another aspect, the subject is a female. In another aspect, the subject is a female of childbearing age. In another aspect the female as delivered a baby within the last 1-12 months. In another aspect, the subject is male.

As used herein, "in need of treatment" and the like refers to a subject that has a disease, condition, or disorder or is suspected of having the disease, condition, or disorder according to various diagnostic criteria typically used in practice, or desires treatment or is indicated for treatment. Thus, "in need of treatment" can include the operation of identifying a subject in need of treatment.

As used herein, "identifying a subject in need of treatment" can include the operation of obtaining a biological sample from the subject and determining the level of one or more biomarkers as described herein, assessing a biological sample obtained from the subject, performing an imaging analysis on the subject, assessing one or more clinical characteristics of the subject (e.g., assessing symptoms or overt symptoms), or a combination thereof.

As used herein, the terms "illness," "disease," "condition," "symptom", and "disorder" can be used interchangeably and refer to an abnormality or incorrect functioning of any part, group, or system of a subject's physiology regardless of the causality thereof. For example, a mental illness or emotional disorder can be caused by environmental factors, genetic factors, physiologic events, past experiences, and other influences or combinations thereof.

As used herein, an "acute" condition refers to a condition that can develop rapidly and have distinct symptoms needing urgent or semi-urgent care. By contrast, a "chronic" condition refers to a condition that is typically slower to develop and lingers or otherwise progresses over time. Some examples of acute conditions can include without limitation, an asthma attack, bronchitis, a heart attack, pneumonia, and the like. Some examples of chronic conditions can include without limitation, arthritis, diabetes, hypertension, dyslipidemia, and the like.

The terms "serum levels," "serum amounts", "serum concentrations," "plasma levels," "plasma concentrations," "blood levels," and "blood concentrations" and the like can be used interchangeably herein and refer to the total amount of an identified analyte (e.g., identified metabolite or active agent), including free, bioavailable, and bound fractions in a subject's blood. For example, "serum allopregnanolone" or "serum allopregnanolone levels" or "serum allopregnanolone concentration" or "plasma allopregnanolone concentration" or "allopregnanolone concentration in the blood" refer the total allopregnanolone concentration which is the sum of the allopregnanolone fractions present including substantially free and bound allopregnanolone concentrations. It should be understood that in this written description, such terms provide express support for total analyte or agent levels, as well as for the various applicable fractions thereof, including bioavailable, bound, and substantially free fractions. Unless otherwise specified, these values are "observed" concentrations or amounts without adjusting or correcting for the base-line serum levels in the subject(s). As with any bio-analytical measure, for increased consistency, the method employed to measure initial serum levels should be consistent with the method used to monitor and re-measure serum levels during clinical testing and therapy for a subject. As used herein, the term "$C_{avg}$," refers to an average serum concentration level for time 0 to t (e.g., average daily serum concentration level, daily $C_{avg}$, is calculated as ratio of $AUC_{0-24}/24$ hours) and the term "$C_{max}$," refers to a maximum serum concentration level post single dose administration for the period.

As use herein with respect to physiologic levels of a given substance, the term "baseline" refers to a level or concentration of the substance, such as analyte of interest (e.g., allopregnanolone), in a subject prior to administration of an active agent. For example, the baseline level of allopregnanolone in a subject would be the subject's allopregnanolone serum level prior (e.g., just prior) to the commencement of allopregnanolone administration or therapy.

The term "oral administration" represents any method of administration in which an active agent can be administered by swallowing, chewing, sucking, or drinking of the composition or dosage form. Oral administration can be intended for enteral delivery of an active agent or transmucosal delivery of the active agent. In some embodiments, the composition and dosage forms of the current disclosure can be admixed with food or drink prior to being orally consumed or can be otherwise co-administered with food or a meal.

As used herein, the terms "release" and "release rate" are used interchangeably to refer to the discharge or liberation of a substance, including without limitation a drug, from the composition or dosage form into a surrounding environment such as an aqueous medium either in vitro or in vivo. In another aspect, the term "disintegration" is a physical process related to the mechanical breakdown of a tablet into smaller particles/granules, representing the breakage of inter-particle interactions generated during formation of a tablet by compaction of granulated particles of the active pharmaceutical ingredient (API) and excipients according to <701>Disintegration, USP 43. In another aspect, the term "disintegration" is a physical process related to the opening or rupturing of a capsule. As used herein, the term "disintegration time" refers to an amount of time required to elapse in order for disintegration to occur.

As used herein, a "dosing regimen" or "regimen" such as an "initial dosing regimen" or "starting dose" or a "maintenance dosing regimen" refers to how, when, how much, and for how long a dose of the compositions or dosage forms of the present disclosure can be administered to a subject. For example, an initial or starting dose regimen for a subject may provide for a total daily dose of from about 10 mg to about 3400 mg administered in divided doses at least 4 hours apart with meals repeated daily for 30 days.

As used herein, "daily dose" refers to the amount of allopregnanolone administered to a subject over a 24-hour period of time. The daily dose can be administered one or more administrations during the 24-hour period. In one embodiment, the daily dose provides for two or three or four or six or eight administrations in a 24-hour period. With this in mind, an "initial dose" or initial daily dose" refers to a dose administered during the initial regimen or period of a dosing regimen.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or by other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986), incorporated herein by reference.

As used herein "single unit" when used to describe dosing of a subject refers to the dosage form being a single dosage form, e.g., a single tablet, capsule, pump or squirt of gel or solution, etc. In contrast, "multiple unit" when used to describe dosing of a subject refers to the dosage including two or more dosage forms, e.g., 2 capsules, 3 tablets, 2-4 pumps or squirts, etc. It is noteworthy that multiple unit dosage forms generally will be the same type of dosage forms (i.e. tablet or capsule) but are not required to be the same dosage form type.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "consisting essentially of" or "consists essentially of" or "essentially consisting" "have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

Occurrences of the phrase "in one embodiment," or "in one aspect," herein do not necessarily all refer to the same embodiment or aspect.

As used herein, comparative terms such as "increased," "decreased," "better," "worse," "higher," "lower," "enhanced," "improved," "maximized," "minimized," and the like refer to a property of a device, component, composition, biologic response, biologic status, or activity that is measurably different from other devices, components, compositions, biologic responses, biologic status, or activities that are in a surrounding or adjacent area, that are similarly situated, that are in a single device or composition or in multiple comparable devices or compositions, that are in a group or class, that are in multiple groups or classes, or as compared to an original (e.g., untreated) or baseline state, or the known state of the art. For example, a composition or dosage form comprising allopregnanolone that "increases" allopregnanolone serum levels or provides an allopregnanolone in a subject that is elevated as compared to a serum level at a previous point in time, such as a baseline level (e.g., prior to treatment), or as compared to an earlier treatment with a different dose (e.g., lower dose). Alternatively, a composition or dosage form that provides an "increased" serum level of allopregnanolone may provide such increase as compared to an alternative known composition or dosage form e.g., compared to an equivalent amount of allopregnanolone utilizing a sub optimal additive or compositions comprising crystalline allopregnanolone or compositions consisting essentially of allopregnanolone suspended/dissolved in edible oil such as canola oil or peanut oil or medium chain triglyceride, or compositions consisting essentially of allopregnanolone solubilized/dissolved allopregnanolone in non-encapsulated aqueous cyclodextrin solution or compositions consisting essentially of allopregnanolone suspended in TWEEN-80 when orally administered the subject.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "fully" refers to the complete extent or degree of an action, characteristic, property, state, structure, item, or result.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range, or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Description

Reference will now be made in detail to preferred invention embodiments. While the embodiments will be described with particularity, the present disclosure is not limited to such embodiments. To the contrary, it is intended to cover alternatives, variants, modifications, and equivalents as may be included within the spirit and scope of the disclosure.

Drawings presented herein are for illustrative purposes only and are not meant to be actual views of any particular oral pharmaceutical composition. Variations in the shapes and profiles depicted in the drawings as a result, for example, of subject variability and/or multicompartmental bioavailability behavior are to be expected. Thus, embodiments described herein are not to be construed as being limited to the particular shapes or profiles as illustrated, but include deviations in shapes that result, for example, from subject variability. For example, a PK curve that is illustrated as a smooth single compartment model curve, may include at least one of subject variability in the PK profile and multiple compartment response. Thus, profiles illustrated in the figures are illustrative in nature, and their shapes are not intended to illustrate the precise shape of a region and do not limit the scope of the present claims. As no scale is presented with the drawings, the drawings are not necessarily to scale.

Exemplary Embodiments

In one embodiment the invention comprises the administration of a composition comprising TD for a subject in need of testosterone intervention independent of their gonadal status-hypogonadal or eugonadal—at pretreatment levels.

In another embodiment the invention comprises the administration of composition comprising TD for a subject in need of testosterone intervention based on a morning baseline testosterone level of at least one of <400, <350, <300, and <250 ng/dL.

In another embodiment the invention comprises methods and compositions to treat/manage liver disease such as NASH, nonalcoholic fatty liver disease, any cholangitis.

In another embodiment the invention comprises methods and compositions to treat/manage an end stage disease such as, advanced kidney disease, end-stage renal disease (ESRD), chronic kidney disease (CKD), liver cirrhosis, chronic liver failure, end stage liver disease (RSLD), cancer, congestive Heart failure (CHF), pulmonary fibrosis, and chronic obstructive pulmonary disease (COPD).

The methods and compositions of this invention result in a favorable benefit to risk profile relative to rifaximin thru fewer adverse events upon oral administration as compared to a comparable rifaximin administration. The methods and compositions of this invention result in a favorable benefit to risk profile relative to oral non-TD comprising compositions thru fewer adverse events upon oral administration as compared to comparable non-TD oral administration.

The methods and compositions of this invention result in no increase in cardiovascular risk or a decrease in cardiovascular risk. The methods and compositions of this invention result no decrease in HDL, an increase in HDL, or an attenuated HDL decrease. The methods and compositions of this invention result no change in blood pressure, an increase in systolic BP of no more than 3 mmHg, or an increase in diastolic BP of no more than 1 mmHg. The methods and compositions of this invention result in a reduction in cardiac inflammation markers such as cardiac reactive protein (CRP). The methods and compositions of this invention result in an improvement in cardiac muscle health (including cardiac atrophy) or a prevention of degradation of cardiac muscle health (including cardiac atrophy).

The methods and compositions of this invention result <5 mg/dL mean reduction in HDL, fewer treated subjects (<20%) had their HDL levels shifted from normal HDL-cholesterol at baseline to below the normal range after a period of testosterone treatment.

The methods and compositions of this invention result in at least 1.0 mm hg lower SBP and/or at least 0.5 hg mm dB relative the methods and compositions of oral TU. The methods and compositions of this invention result in less (by 1 mg/dL) mean reduction in HDL relative to TU or non TD methods and compositions. The methods and compositions of this invention result in 10% fewer treated subjects have their HDL levels shifted from normal HDL-cholesterol at baseline to below the normal range after a period of testosterone treatment relative to TU or non TD methods and compositions.

The methods and compositions of this invention result in maintaining prostate health, prevent deterioration of prostate health, attenuate in BPH symptoms increase, no increase in BPH symptoms, and no change in prostate size or weight.

The methods and compositions of this invention reduce the potential occurrences of benign prostrate hyperplasia and/or prostate weight or size increase by at least 5% relative to TU and non-TD method and compositions. The methods and compositions of this invention reduce the potential extent of prostate weight or size increase by at least 5% relative to TU and non-TD methods and compositions. The methods and compositions of this invention reduce, such as by at least 5%, prostate weight to body weight ratio, response markers of testosterone induced prostatic hyperplasia relative to other forms of T therapy, including TU.

The methods and compositions of this invention result in lower infection rates, such as by at least 5%, relative to TU and non-TD methods and compositions.

The methods and compositions of this invention result in maintaining or preventing further deterioration of muscle, heart, lung, kidney, brain, liver or any organ health, such as by at least 5%, relative to TU and non-TD methods and compositions.

Liver disease such as NASH and end stage disease such as cirrhosis is typically associated with chronic inflammation of various biological tissues. Accordingly, the methods and compositions of this invention reduce inflammation and inflammation markers such as CRP, pro inflammatory cytokines such as TNF-alpha, interleukins, such as by at least 5%, relative to TU and non-TD methods and compositions.

Patients with cirrhosis are in a state of immune dysfunction and are at high risk of developing serious infections. Bacterial infections remain the most common cause of morbidity and mortality in these patients. The most prevalent infections in patients with cirrhosis are spontaneous bacterial peritonitis and urinary tract infections followed by pneumonia, spontaneous bacteremia, skin and soft tissue infections, and *Clostridium difficile* infection (CDI), with variations in the risk of death. The major causative organisms are gram-negative bacteria, e.g., *E. coli*, *Klebsiella* spp. and *Enterobacter* spp., whereas gram-positive bacteria, especially Enterococci and *Staphylococcus aureus*, comprise about 20% and anaerobes only 3%.

In one aspect, the methods and compositions of this invention provide for immunomodulation, decreased mortality and/or morbidity, lower infection rate than a placebo, protection against gram-negative bacteria such as *E. coli*, protection against gram-positive bacteria, decreased hospital admissions, and lower incidences of at least one of: spontaneous bacterial peritonitis, urinary tract infections, pneumonia, spontaneous bacteremia, skin and soft tissue infections, and *Clostridium difficile* infection (CDI).

In another aspect the methods and compositions of this invention, the metabolite TD is antibacterial and lowers infection rates, lowers ammonia levels in a subject, and improves cognitive function. In an aspect of the methods and compositions of this invention, the TD is a pro-antibacterial agent.

Anemia is a condition in which a subject lacks enough healthy red blood cells to carry adequate oxygen to his body's tissues. Anemia, also referred to as low hemoglobin, can make one feel tired and weak. Prevalence of anemia is common in end stage cirrhotic patients and is a predictor of overt or minimal Hepatic Encephalopathy (HE) in cirrhotic liver transplant candidates. In an aspect, in such patients the methods and compositions of this invention exhibit erythropoietic effects, lowers anemia, prevents further decline in hemoglobin, increases hematocrit by at least 3% or hemoglobin value by at least about 1 g/dL.

Endocrine dysfunction is quite common in patients with end stage disease. The hypothalamus-pituitary-gonadal axis is profoundly altered in advanced cirrhotic patients, leading to endocrine dysfunction with increased serum aromatase activity. Men with chronic non-alcoholic liver disease had reduced levels of total and free testosterone and increased levels of SHBG compared with controls with normal liver function. Low total testosterone can also be an independent risk factor for major infections and mortality. Moreover, often used Spironolactone treatment to manage cirrhosis is often associated with decreased circulating testosterone levels.

In an aspect the methods and compositions of this invention improve/counter endocrine dysfunction, increase total testosterone, reverse anti-androgenic effects of spironolactone, increase sex hormone binding globulin and increase free testosterone. In an aspect, the methods and compositions of this invention normalize abnormal free T, total T and SHBG individually or simultaneously. In an aspect, the methods and compositions of this invention increase free T by at least about 20%, increase total T $C_{avg}$ by at least about 100 ng/dL, and lower SHBG by at least about 20%.

In an aspect, the methods and compositions of this invention provides antioxidation effects resulting in improved reactive oxygen species levels and improved mitochondrial function.

Albumin is predominantly synthesized in the liver. Patients with cirrhosis have impaired hepatocellular function and reduced albumin synthesis, which can reach a 60-80% reduction in advanced cirrhosis. Moreover, low serum albumin level can be a clinical biomarker associated with impaired cognitive function. Conventionally, hypoalbuminemia in adults is defined by a decreased serum ALB level of <35 g/l, and clinically significant hypoalbuminemia may be identified by a serum ALB level of <25 g/l. A serum ALB level≤31.6 g/l may be associated with higher risk of development of overt HE, and a serum ALB level≤22.8 g/l may be associated with higher risk of in-hospital death from overt HE. A 0.5 mg/dL increase in albumin could result significant decrease in mortality.

In an aspect, the methods and compositions of this invention provides antioxidation effects resulting in stimulating albumin production, treating hypoalbuminemia, modulating protein homeostasis or proteostasis, inhibits proteolysis, increases albumin by at least 0.5 mg/dL without exogenous albumin administration, improves cognition function, lowers or results in no occurrence of HE events, decreases hospital admissions, decreases mortality, and improves survival.

Muscle disorder in form of sarcopenia, frailty, or myosteatosis along with cachexia is highly prevalent in an end stage disease. Fat-free mass depletion are predictors of HE in cirrhotic liver transplant candidates. Sarcopenia contributes to frailty and increases the risk of minimal and overt hepatic encephalopathy (HE). Clinically overt HE is significantly higher in cirrhotic patients with muscle depletion or decreased muscle strength.

Myostatin is a naturally occurring regulatory protein of the TGF-beta family of growth factors known to negatively regulate, or inhibit, muscle growth. Myostatin is a critical regulator of protein synthesis, muscle loss, bone density and is common in patients with cirrhosis. Osteopenia, high alkaline phosphatase (ALP) and osteoporosis are highly prevalent in individuals with liver cirrhosis.

In an aspect, the methods and compositions of this invention result in improvement or reversal of sarcopenia, improvement or prevention of worsening of sarcopenia secondary to ESD, frailty, myosteatosis, cachexia, prevention/lowering of risk of muscle toxicity, inhibition of myostatin, increased lean mass, increased muscle mass, reduced fat mass, increased lean mass and reduced fat mass, enhanced muscle protein synthesis, prevention of muscle wasting, improved appetite, increased IGF-1 and mTOR activation, increased sustained satellite cell activity, suppressed myostatin secretion and signaling, increased lean mass by at least one of 1 kg, 2 kg, and 3 kg, and/or decreased fat mass by at least one of 1 kg, 2 kg, and 3 kg, improved or prevented deterioration in liver frailty index, improved handgrip, improved grip strength, improved (increased) 6 min walking distance, lowered myosteatosis, and reduced muscle fat by at least about 10% relative to a placebo administration or a baseline.

In an aspect, the methods and compositions of this invention result in improvement in bone health, prevention or reduction in further deterioration of osteopenia, lowering of ALP, and reduction in further deterioration of osteopenia.

In an aspect, the methods and compositions of this invention reduce the occurrence of decompensation events while improving body composition thru improvement in lean mass or reduction in fat mass, and/or improvement in liver function.

In an aspect, the methods and compositions of this invention in patients with chronic liver disease provides resolution of NASH, reduce hepatic steatosis, resolved or lowered ballooning, reduced or lowered inflammation, lowered portal hypertension, lowered portal hypertension by at least about 2 mm hg, reduced key liver injury markers such as reduced ALT, AST, GGT, ALP, lowered and sustained lowering of ALT, AST, GGT, ALP, normalization of ALT, AST, GGT, ALP, and lowering of abnormal ALT, AST, GGT, ALP levels. Liver markers are lowered in as early as four weeks, and by at least about a 10% reduction from a baseline or a placebo administration adjusted.

In an aspect, the methods and compositions of this invention provide in cirrhotic patients, a reduction in HbA1c such as an ~0.2-unit reduction in HbA1c.

In an aspect, the methods and compositions of this invention provides sexual and mental domain functions in patients.

In an aspect, the methods and compositions of this invention halt a hypermetabolic state, improve anabolic effects, provide anticatabolic effects, increase muscle protein synthesis, and decrease skeletal muscle protein breakdown.

Lower systemic ammonia via improving ammonia detoxification: Cirrhotic patients have elevated levels of plasma and skeletal muscle ammonia, a neurotoxin and a myotoxin, which correlate with decreased muscle mass and increased myostatin expression.

Hyperammonemia is a consistent abnormality that occurs in cirrhosis due to reduced urea synthesis that occurs almost exclusively in the liver because of hepatocellular dysfunction with or without portosystemic shunting. Excess ammonia is a pivotal cause of muscle loss and functional impairment in cirrhosis. Hyperammonemia in vivo induces myostatin and reduces skeletal muscle mass. Hyperammonemia also activates skeletal muscle proteolysis by autophagy and upregulates myostatin expression that impairs protein synthesis.

Ammonia is detoxified in the liver through the urea cycle, and the skeletal muscle is an alternate organ for ammonia detoxification. Therefore, in the setting of liver disease, reduced capacity to remove ammonia in the liver, aggregated with muscle mass depletion, further reduces the body's capacity to clear ammonia, which in turn leads to a higher risk of developing hyperammonemia and hepatic encephalopathy (HE). Muscles play a significant compensatory role in detoxifying ammonia during liver disease since it houses the enzyme glutamine synthetase (GS), an important ammonia-removing pathway during the amination of glutamate to glutamine.

Lower ammonia thru decreased ammonia production thru antibacterial effects: In patients with cirrhosis, specific organism in the gastrointestinal tract can cause an increase in ammonia leading to increased HE risk. The largest amounts of ammonia are generated by gram-negative anaerobes while gram-positive non-sporing anaerobes form modest amounts of ammonia in vivo from peptides and amino acids. Patients with cirrhosis are at high risk of *Clostridium difficile* infection (CDI)—a source for an increase in systemic ammonia resulting in hyperammonemia.

TD, a reversible dodecanoic acid ester of testosterone, is believed to exhibit antibacterial activity against gram-negative anaerobes and gram-positive non-sporing anaerobes, primarily attributed to the esterase hydrolysis product, dodecanoic acid. These specific organisms in the gastrointestinal tract can produce amounts of ammonia in vivo from peptides and amino acids ammonia resulting in a systemic increase and leading to increased HE risk.

In an aspect, the methods and compositions of this invention lower systemic ammonia levels or counter hyperammonemia or lower HE events in patients with cirrhosis. Via antibacterial activity against gram-negative bacteria in the GI tract, or gram-negative and gram-positive bacteria in the GI tract, the methods and compositions of this invention favorably regulate the structure and function of intestinal bacteria, cause a decrease in abundance of *Veillonella, Haemophilus, Streptococcus*, Parabacteroides, Megamonas, *Roseburia*, Alistipes, Ruminococcus, *Lactobacillus*, and *Clostridium difficile, E. coli*.

In an aspect, the methods and compositions of this invention lower systemic ammonia levels, counter hyperammonemia by restoring/improving organ ammonia detoxification function, restoring/improving liver and/or muscle organ ammonia detoxification function, counter proteolysis via autophagy, myostatin inhibition, improve skeletal muscle mass through systemic ammonia level lowering, and improve cognitive function, normalization or lowering of ALP, and lowering of abnormal ALP.

In an aspect the methods and compositions of this invention lower systemic ammonia levels, counter hyperammonemia with decrease ammonia production and/or, restore/improve organ ammonia detoxification function, restore/improve liver and/or muscle organ ammonia detoxification function.

In an aspect, the methods and compositions of this invention resolve hepatic ballooning, improve hepatic steatosis, improve hepatic inflammation, stimulate liver regeneration, improve fibrosis, and prevent worsening of fibrosis in patients with chronic liver disease.

Rifaximin, an approved treatment for HE, has a very low gastrointestinal absorption with antibacterial activity.

In an aspect, the methods and compositions of this invention lower systemic ammonia levels through achieving significant systemic levels of a therapeutic agent. In an aspect, the methods and compositions of this invention lower systemic ammonia levels while improving muscle mass & liver function, and without prostrate and cardiovascular risk. In an aspect, the methods and compositions of this invention do not appreciably inhibit P-glycoprotein transporter.

In an aspect, the methods and compositions of this invention function as a prophylaxis to prevent or lower risk of HE, reduction in risk of overt hepatic encephalopathy recurrence, reduction in breakthrough episodes, reduced HE-related hospitalizations (hospitalizations directly resulting from HE, reduce hospitalizations complicated by HE), delay time to onset of episode of overt HE, ascites occurrence of <10% in groups of HE subjects, asterixis improvement, mental status improvement, intellectual function improvement, improvement in psychometric/neurophysiologic tests, higher HE reversal, and lower death in groups of HE subjects.

In an aspect, the methods and compositions of this invention result in a reduction in HE-related hospitalization, a reduction in any decompensated event related hospitalization, a reduction in all-cause hospitalization, improved survival rates, reduced hospital admissions, and improved QOL.

In an aspect, the methods and compositions of this invention treat/manage liver cirrhosis of various etiologies including alcoholic, non-alcoholic fatty liver disease, viral hepatitis, substance abuse, immune disorder.

In an aspect, the methods and compositions of this invention treat/manage liver cirrhosis resulting in lower mortality rates or improved survival rates among groups of patients.

In an aspect, the methods and compositions of this invention treat/manage liver cirrhosis in cirrhotic patients with at least one of: minimal HE and a prior history of overt HE, sarcopenia, hyponatremia, epilepsy, type 2 diabetes, a high creatinine level, a high bilirubin level, and a low albumin level.

In an aspect, the methods and compositions of this invention treat/manage liver Cirrhosis in subjects with decompensated cirrhosis on a liver transplant wait list, having had at least one previous decompensation event; having had at least one previous HE decompensation event, having had at least one previous ascites decompensation event, having a MELD score of at least one of greater than 12, less than 20, and from about 12 to about 20.

In an aspect, the methods and compositions of this invention treat/manage liver cirrhosis in subjects that are sarcopenic, have skeletal mass index of L3 SMI to be less than 53 (cm2/m2).

In an aspect, the methods and compositions of this invention treat/manage liver cirrhosis in subjects that are frail, have a Liver Frailty Index of greater than 3.2.

In an aspect, the methods and compositions of this invention treat/manage liver cirrhosis in subjects that have myosteatosis, and have muscle fat as assessed by CT scan to be at least about 10%.

In an aspect, the methods and compositions of this invention lower or prevent an increase of a MELD score In an aspect, the methods and compositions of this invention improve post-transplant outcomes, improve post-transplant survival rates, and lower post-transplant rehabilitation requirements/costs.

In one aspect, the methods and compositions of this invention mitigate ascites and improve survival rates of cirrhotic patients with refractory ascites.

In an aspect, the methods and compositions of this invention may decrease the occurrence of HE events for a subject. By way of example, when comparing treatment to placebo, the hazard ratio for HE events may include about or less than 0.75, 0.6, 0.5, 0.4, 0.25, 0.2 and 0.1. By way of example only, the hazard ratio for HE events may be about 0.27.

In an aspect, the methods and compositions of this invention may increase a subjects L3-SMI. By way of example, a subject L3-SMI increase may include about or greater than 0.25 cm$^2$ m$^{-2}$, 0.5 cm$^2$ m$^{-2}$, 0.75 cm$^2$ m$^{-2}$, 1 cm$^2$ m$^{-2}$, 1.5 cm$^2$ m$^{-2}$, 2 cm$^2$ m$^{-2}$, 2.5 cm$^2$ m$^{-2}$, 3 cm$^2$ m$^{-2}$, 4 cm$^2$ m$^{-2}$, 5 cm$^2$ m$^{-2}$, 7.5 cm$^2$ m$^{-2}$, and 10 cm$^2$ m$^{-2}$. By way of example only, subject L3-SMI increase may be about 3.6 cm$^2$ m$^{-2}$. By way of another example, subject L3-SMI increase may be about 2.6 cm$^2$ m$^{-2}$.

In an aspect, the methods and compositions of this invention may increase a subjects L3-SMI. By way of example, a subject L3-SMI increase when compared to placebo may include about or greater than 0.25 cm$^2$ m$^{-2}$, 0.5 cm$^2$ m$^{-2}$, 0.75 cm$^2$ m$^{-2}$, 1 cm$^2$ m$^{-2}$, 1.5 cm$^2$ m$^{-2}$, 2 cm$^2$ m$^{-2}$, 2.5 cm$^2$ m$^{-2}$, 3 cm$^2$ m$^{-2}$, 4 cm$^2$ m$^{-2}$, 5 cm$^2$ m$^{-2}$, 7.5 cm$^2$ m$^{-2}$, and 10 cm$^2$ m$^{-2}$. By way of example only, subject L3-SMI increase may be about 4.4 cm$^2$ m$^{-2}$.

In an aspect, the methods and compositions of this invention may increase a subjects L3-SMI in a time period. By way of example a subject L3-SMI increase time period may include about or less than 4 weeks, 6 weeks, 8 weeks, 12 weeks, 16 weeks, 20 weeks, 24 weeks, 30 weeks, 36 weeks, 40 weeks, 48 weeks, and 52 weeks. By way of example only, subject L3-SMI increase time period may be about 12 weeks. By way of another example, subject L3-SMI increase time period may be about 24 weeks.

In an aspect, the methods and compositions of this invention may decrease a subjects weight and increase a subjects L3-SMI. By way of example, a subjects weight decrease may include about or greater than 5%, 10%, 15%, 20%, 25%, and 30% w/w %. By way of example, a subjects L3-SMI increase may include about or greater than 0.25 cm$^2$ m$^{-2}$, 0.5 cm$^2$ m$^{-2}$, 0.75 cm$^2$ m$^{-2}$, 1 cm$^2$ m$^{-2}$, 1.5 cm$^2$ m$^{-2}$, 2 cm$^2$ m$^{-2}$, 2.5 cm$^2$ m$^{-2}$, 3 cm$^2$ m$^{-2}$, 4 cm$^2$ m$^{-2}$, 5 cm$^2$ m$^{-2}$, 7.5 cm$^2$ m$^{-2}$, and 10 cm$^2$ m$^{-2}$. By way of example only, subject weight decrease may be about 20% and subject L3-SMI increase may be about 3.6 cm$^2$ m$^{-2}$.

In an aspect, the methods and compositions of this invention may achieve a subject PGI-C score that includes at or less than 4, 3, 2, and 1. By way of example, the PGI-C score may be 3.

In an aspect, the methods and compositions of this invention may achieve a subject PGI-C in a time period. By way of example a subject PGI-C time period may include about or less than 4 weeks, 6 weeks, 8 weeks, 12 weeks, 16 weeks, 20 weeks, 24 weeks, 30 weeks, 36 weeks, 40 weeks, 48 weeks, and 52 weeks. By way of example only, subject PGI-C time period may be about 4 weeks. By way of another example, subject PGI-C time period may be about 12 weeks. By way of another example, subject PGI-C time period may be about 24 weeks.

Compositions, additives, and dosage forms of the instant invention encompass that disclosed in the patent incorporated herein.

Exemplary excipients include: A lipophilic surfactant to hydrophilic surfactant ratio of: >2;1, >3:1, >3.5:1, >5;1, >6:1, >8:1, and >10:1. A fatty acid/hydrophilic surfactant ratio of: >0.3:1, >1;1 >2; 1, >3:1, >3.5:1, >5;1, >6:1, >8:1, and >10:1. A hydrophilic surfactant of: <20%, <15%, <12%, <10%, and <5%. A TD loading of 27-32% and having a TD/fatty acid ratio w/w % of: >0.4, >1, >1.67, >2.0,>3, >4, >5, and >6. A TD loading of 27-32% and having a TD/hydrophilic surfactant ratio w/w % of: >1.67, >2.0,>3, >4, >5, and >6. A TD loading of 27-32% and having a TD/hydrophilic surfactant ratio w/w % f: >1.67, >5, >25, >50, and >75, and the fatty acid amount is >40%, >45%, >50%>55%, >60%, >65%, and >70%. A TD loading of 20-35% with at least 50% of a fatty acid (such as oleic acid, lauric acid).

Exemplary dosing regimens include: A daily dose of 200 mg to 1500 mg/day. A dosing frequency of BID or QD. A chronic and sub chronic use (up to 1 year).

Exemplary blood levels include: A $C_{avg}$ of 350 ng/ml to 1080 ng/dL. A change in $C_{avg}$ from baseline of 100 ng/dL.

Exemplary markers of the instant invention (preferably relative to pretreatment or a placebo administration) include: A decrease in SHBG by at least about 10%. A lower portal hypertension value by at least about 2 mmHG. At least about a 0.5 mg/dl increase in albumin. A lower Liver frailty index (LFI) by at least about 0.2 units. An increased L2 muscle mass by at least about 5%. A reduce muscle fat (lower myosteatosis) value of at least about 10%. A lower systemic ammonia. A lowering of abnormal level of at least one of ALT, AST, GGT, and ALP by at least about 10%. An increase of lean mass by at least one of about 1 kg, about 2 kg, and about 3 kg, and/or a decrease in fat mass by at least one of about 1 kg, about 2 kg, and about 3 kg. An increase in free T by at least about 20%. An increase in total T $C_{avg}$ by at least about 100 ng/dL. An increase in hematocrit by at least about 3% or an increase in a hemoglobin value by at least about 1 g/dL. A lower inflammation marker.

The methods and compositions of this invention result in about <5 mg/dL mean reduction in HDL, fewer treated subjects (<20%) that had their HDL levels shifted from normal HDL-cholesterol at baseline to below the normal range after a period of testosterone treatment.

Exemplary markers of the instant invention (preferably relative to a comparable administration of a non-TD testosterone ester) include: A reduction in the potential occurrences of benign prostrate hyperplasia. A reduction in prostate weight or an increase in prostate size by at least about 5%. A reduction in an HbAlc level by at least about 0.2 units. A lower SBP by at least about 1 mm Hg and a lower DBP by at least about 0.5 mmHg. A mean reduction in HDL by at least about 1 mg/dL. A higher amount of bacterial inhibition activity. A higher proportion of participants of treatment experiencing moderately better or much better response in patient's global impression of change (PGI-C) such as a proportion of at least one of at least about 20%, at least about 30%, at least about 40%, at least about 50%, at least about 60%, and at least about 70%. An improvement in MSI of at least about 3 $cm^2/m^2$ (relative to placebo or baseline) after at least 3 months of treatment.

EXAMPLES

TABLE A

Testosterone dodecanoate compositions comprising lipophilic additive*

| Component | % w/w |
|---|---|
| Testosterone Dodecanoate | 20-45 |
| Lipophilic additive (e.g., glyceryl fatty acid ester, glyceryl fatty acid ester, polyglycerol fatty acid ester, mono glyceride, diglyceride, triglyceride, propylene glycol fatty acid ester, glyceryl monocaprylocaprate, glyceryl monocaprylate, glycerides of coconut oil, α-tocopherol or its derivative, sterol or its derivatives, sorbitan fatty acid esters, fatty acids, fatty acid derivatives, edible oils, etc.) | 55-80 |
| Other ingredients | q.s. |

*Lipophilic additive can be a surfactant or a non-surfactant

TABLE A1

Testosterone dodecanoate compositions comprising lipophilic additive

| | Ingredient | Composition (w/w %) | | |
|---|---|---|---|---|
| | | 1 | 2 | 3 |
| | Testosterone Dodecanoate | 23-36 | 26-33 | 28-32 |
| Additives | Lipophilic additive (e.g., glyceryl fatty acid ester, glyceryl fatty acid ester, polyglycerol fatty acid ester, mono glyceride, diglyceride, triglyceride, propylene glycol fatty acid ester, glyceryl monocaprylocaprate, glyceryl monocaprylate, glycerides of coconut oil, α-tocopherol, tocotrienol or its derivative, sterol or its derivatives, sorbitan fatty acid esters, fatty acids, fatty acid derivatives, edible oils, etc.) | 40-70 | 45-60 | 45-65 |
| | Other ingredients* | q.s. | q.s. | q.s. |

*Other ingredients can comprise, but not limited to, co-solvent, antioxidant, permeation enhancer, stabilizer, plasticizer, solidifier, preservative, and so on

TABLE B

Testosterone dodecanoate compositions comprising fatty acid or fatty acid derivative or fatty acid comprising lipophilic additive

| Component | w/w % |
|---|---|
| Testosterone Dodecanoate | 20-45 |
| Fatty Acid (e.g., Oleic, Lauric acid, Stearic acid) or fatty acid derivative (e.g. glycerol monolaurate, sorbitan monolaurate, sorbitan monooleate, monolaurin, dilaurin, trilaurin, diolein, triolein, sodium lauryl sulfate, lauryl sulfate, glyceryl Di stearate, propylene | 50-80 |

TABLE B-continued

Testosterone dodecanoate compositions comprising fatty acid or fatty acid derivative or fatty acid comprising lipophilic additive

| Component | w/w % |
|---|---|
| glycol monolaurate) fatty acid comprising lipophilic additive (e.g. coconut oil, laurel oil, and palm kernel oil) | |
| Other ingredients | q.s. |

TABLE B1

Testosterone dodecanoate compositions comprising Fatty Acid

| | Ingredient | Composition (w/w %) | | |
|---|---|---|---|---|
| | | 1 | 2 | 3 |
| Additives | Testosterone Dodecanoate | 23-36 | 26-33 | 28-32 |
| | Fatty Acid (e.g., Oleic, Lauric acid, Stearic acid) | 50-75 | 53-70 | 55-65 |
| | Other ingredients* | q.s. | q.s. | q.s. |

TABLE C

Testosterone dodecanoate compositions comprising hydrophilic additive*

| Component | w/w % |
|---|---|
| Testosterone Dodecanoate | 20-45 |
| Hydrophilic additives (e.g., hydrogenated polyoxyl vegetable oil or glyceride, PEG glyceride of fatty acid ester, polyglycerol-10 fatty acid ester, polysorbate 20,, poloxamer, polysorbate 80, polyoxyl 40 hydrogenated castor oil, Polyoxyl 35 castor oil, sodium lauryl sulfate, sodium docusate, poloxamer, polyethylene glycol 1000 tocopherol succinate, PEG) | 0.1-45 |
| Other ingredients | q.s. |

*Hydrophilic additive can be a surfactant and a non-surfactant

TABLE C1

Testosterone dodecanoate compositions comprising hydrophilic additive

| | Ingredient | Composition (w/w %) | | |
|---|---|---|---|---|
| | | 1 | 2 | 3 |
| Additives | Testosterone Dodecanoate | 23-36 | 26-33 | 28-32 |
| | Hydrophilic additives (e.g., hydrogenated polyoxyl vegetable oil or glyceride, PEG glyceride of fatty acid ester, polyglycerol-10 fatty acid ester, polysorbate 20,, poloxamer, polysorbate 80, polyoxyl 40 hydrogenated castor oil, Polyoxyl 35 castor oil, sodium lauryl sulfate, sodium docusate, poloxamer, polyethylene glycol 1000 tocopherol succinate, PEG) | 0.1-20 | 0.1-12 | 0.1-4.5 |
| | Other ingredients* | q.s. | q.s. | q.s. |

TABLE D

Testosterone dodecanoate compositions comprising hydrophilic additive and lipophilic additive

| Component | w/w % |
|---|---|
| Testosterone Dodecanoate | 20-45 |
| Lipophilic additive (e.g., glyceryl fatty acid ester, glyceryl fatty acid ester, polyglycerol fatty acid ester, mono glyceride, diglyceride, triglyceride, propylene glycol fatty acid ester, glyceryl monocaprylocaprate, glyceryl monocaprylate, glycerides of coconut oil, α-tocopherol or its derivative, sterol or its derivatives, sorbitan fatty acid esters, fatty acids, fatty acid derivatives, edible oils, etc.) | 50-80 |
| Hydrophilic additives (e.g., hydrogenated polyoxyl vegetable oil or glyceride, PEG glyceride of fatty acid ester, polyglycerol-10 fatty acid ester, polysorbate 20,, poloxamer, polysorbate 80, polyoxyl 40 hydrogenated castor oil, Polyoxyl 35 castor oil, sodium lauryl sulfate, sodium docusate, poloxamer, polyethylene glycol 1000 tocopherol succinate, PEG) | 0.1-25 |
| Other ingredients | q.s. |

TABLE D1

Testosterone dodecanoate compositions comprising hydrophilic additive and lipophilic additive

| | Ingredient | Composition (w/w %) | | |
|---|---|---|---|---|
| | | 1 | 2 | 3 |
| Additives | Testosterone Dodecanoate | 23-36 | 26-33 | 28-32 |
| | Lipophilic additive (e.g., glyceryl fatty acid ester, glyceryl fatty acid ester, polyglycerol fatty acid ester, mono glyceride, diglyceride, triglyceride, propylene glycol fatty acid ester, glyceryl monocaprylocaprate, glyceryl monocaprylate, glycerides of coconut oil, α-tocopherol, tocotrienol or its derivative, sterol or its derivatives, sorbitan fatty acid esters, fatty acids, fatty acid derivatives, edible oils, etc.) | 50-75 | 53-70 | 55-65 |
| | Hydrophilic additives (e.g., hydrogenated polyoxyl vegetable oil or glyceride, PEG glyceride of fatty acid ester, polyglycerol-10 fatty acid ester, polysorbate 20,, poloxamer, polysorbate 80, polyoxyl 40 hydrogenated castor oil, Polyoxyl 35 castor oil, sodium lauryl sulfate, sodium docusate, poloxamer, polyethylene glycol 1000 tocopherol succinate, PEG) | 0.5-20 | 0.5-12 | 0.5-4.5 |
| | Other ingredients* | q.s. | q.s. | q.s. |

TABLE E

Testosterone dodecanoate compositions comprising hydrophilic additive and Fatty Acid or Fatty Acid generating/comprising additives

| Component | w/w % |
|---|---|
| Testosterone Dodecanoate | 20-45 |
| Hydrophilic additives (e.g., hydrogenated polyoxyl vegetable oil or glyceride, PEG glyceride of fatty acid ester, polyglycerol-10 fatty acid ester, polysorbate 20,, poloxamer, polysorbate 80, polyoxyl 40 hydrogenated castor oil, Polyoxyl 35 castor oil, sodium lauryl sulfate, sodium docusate, poloxamer, polyethylene glycol 1000 tocopherol succinate, PEG) | 0.5-20 |
| Fatty Acid (e.g., Oleic, Lauric acid, Stearic acid) or fatty acid derivative (e.g. glycerol monolaurate, sorbitan monolaurate, sorbitan monooleate, monolaurin, dilaurin, trilaurin, diolein, triolein, sodium lauryl sulfate, lauryl sulfate, glyceryl Di stearate, propylene glycol monolaurate) fatty acid comprising lipophilic additive (e.g. coconut oil, laurel oil, and palm kernel oil) | 55-80 |
| Other ingredients* | q.s. |

TABLE E1

Testosterone dodecanoate compositions comprising hydrophilic additive and Fatty Acid or Fatty Acid generating/comprising additives

| Ingredient | Composition (w/w %) | | |
|---|---|---|---|
| | 1 | 2 | 3 |
| Testosterone Dodecanoate | 23-36 | 26-33 | 28-32 |
| Additives Fatty Acid (e.g., Oleic, Lauric acid, Stearic acid) or fatty acid derivative (e.g. glycerol monolaurate, sorbitan monolaurate, sorbitan monooleate, monolaurin, dilaurin, trilaurin, diolein, triolein, sodium lauryl sulfate, lauryl sulfate, glyceryl Di stearate, propylene glycol monolaurate) fatty acid comprising lipophilic additive (e.g. coconut oil, laurel oil, and palm kernel oil) | 40-80 | 50-70 | 55-65 |
| Hydrophilic additives (e.g., hydrogenated polyoxyl vegetable oil or glyceride, PEG glyceride of fatty acid ester, polyglycerol-10 fatty acid ester, polysorbate 20,, poloxamer, polysorbate 80, polyoxyl 40 hydrogenated castor oil, Polyoxyl 35 castor oil, sodium lauryl sulfate, sodium docusate, poloxamer, polyethylene glycol 1000 tocopherol succinate, PEG)) | 0.5-20 | 0.5-12 | 0.5-4.5 |
| Other ingredients* | q.s. | q.s. | q.s. |

TABLE F

Compositions comprising Testosterone Dodecanoate

| Component | ~w/w % | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Testosterone Dodecanoate | 31 | 31 | 31 | 29 | 29 | 29 | 29 | 29 | 27 | 27 | 27 | 25 | 25 | 25 |
| Oleic acid | | | 50 | 60 | | 50 | | 55 | 35 | | | 45 | | 60 |
| Stearic acid | 3 | 4 | 8 | | 4 | | 4 | 4 | | 8 | | | 4 | |
| Lauric acid | | | | | | | 10 | | | | 30 | | | |
| Coconut oil | | | | | | | | | | | | | 30 | |
| Glyceryl Palmitosterate | 8 | | | | 10 | 8 | 8 | 8 | | | 11 | | | 5 |
| Sorbitan Monolaurate | | 8 | 10 | | | | | | | | | | | |
| Glycerol laurate (e.g., glycerol mono-, di-, tri- laurate) | | | | 4 | | | | | 15 | 45 | | | | |
| Propylene Glycol laurates (e.g., Propylene Glycol mono- and di- laurate) | | | | | 22 | | | | | | | | | |
| Propylene Glycol Monocaprylate | 25 | | | | 25 | | 25 | | 15 | | | 25 | | |
| Medium Chain Mono- and Diglycerides | 25 | 44 | | | | | 10 | | | | 30 | | 30 | |
| Polysorbate 80 | | | | 6 | | | 12 | | | | | | | |
| TPGS | | 12 | | | | | | | 4 | | | | | |
| Polyoxyl 35 Castor Oil | 8 | | 0.5 | | | 11 | | 4 | | 8 | 12 | 4 | 10 | 9 |
| PEG-40 Hydrogenated Castor Oil | | | | 9 | | | | | | | | | | |
| Other additives (e.g., solidifier, antioxidant, etc.) | q.s. | q.s. | q.s. | q.s. | q.s. | q.s. | q.s. | q.s. | q.s. | q.s. | q.s. | q.s. | q.s. | q.s. |
| Lipophilic additive to hydrophilic surfactant ratio | 7.6 | 5.5 | 136 | 10.7 | 6.7 | 5.3 | 4.8 | 15.8 | 17 | 8 | 5 | 17.5 | 6.4 | 7.2 |
| Fatty acid/hydrophilic surfactant ratio | 0.4 | 0.3 | 116 | 10 | 0.4 | 4.5 | 1.2 | 14 | 9.5 | 1 | 2.5 | 11 | 0.4 | 6.7 |
| TD/fatty acid ratio | 10 | 7.8 | 0.5 | 0.5 | 7.3 | 0.6 | 2 | 0.5 | 0.7 | 3.4 | 0.9 | 0.6 | 6.3 | 0.42 |
| TD/hydrophilic surfactant ratio | 3.9 | 2.6 | 62 | 4.8 | 3.2 | 2.6 | 2.4 | 7.25 | 6.8 | 3.8 | 2.3 | 6.3 | 2.5 | 2.8 |

TABLE F-continued

Compositions comprising Testosterone Dodecanoate

| Component | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| TD form at manufacture Undissolved crystals | yes | yes | no | no | yes | yes | yes | no | no | yes | yes | no | yes | no |
| Physical stability* upon storage at RT for 1 month (U = unstable, S = stable) | U | U | S | S | U | U | U | S | S | U | U | S | U | S |

*Significant presence of drug crystals/crystal growth

TABLE G

Compositions comprising a non-TD

| Component | w/w % |
|---|---|
| Testosterone Undecanoate | 10-20 |
| Lipophilic Additive: (glyceryl monolinoleate, phytosterol, oleic acid, propylene glycol mono laurate) | 55-70 |
| Hydrophilic Additive: PEG-40 Hydrogenated Castor Oil | 14-16 |
| Other ingredients | q.s. |

TABLE G1

Compositions comprising TU

| Component | w/w % |
|---|---|
| Testosterone Undecanoate | 19.8 |
| Oleic acid | 52 |
| Borage oil | 10 |
| Peppermint oil | 2 |
| PEG-40 Hydrogenated Castor Oil | 16 |
| Other additives (e.g., solidifier, antioxidant, etc.) | q.s. |
| Lipophilic additive to hydrophilic surfactant ratio | 4.0 |
| Fatty acid/hydrophilic surfactant ratio | 3.3 |
| TU/fatty acid ratio | 0.38 |
| TU/hydrophilic surfactant ratio | 1.23 |

Suitable additives utilized in various embodiments described herein include, by way of non-limiting example, adsorbing agents, anti-adherents, anticoagulants, antifoaming agents, antioxidants, anti-caking agents, anti-static agents, binders, bile acids, bufferants, bulking agents, chelating agents, coagulants, colorants, co-solvent, opaquants, congealing agents, coolants, cryoprotectants, diluents, dehumidifying agents, desiccants, desensitizers, disintegrants, dispersing agents, enzyme inhibitors, glidants, fillers, hydrating agent, super disintegrants, gums, mucilages, hydrogen bonding agents, enzymes, flavorants, humectants, humidifying agents, lubricant oils, ion-exchange resins, lubricants, plasticizers, pH modifying agents, preservatives, solidifying agent (solidifier), solvents, solubilizers, spreading agent sweeteners, stabilizers, surface area enhancing agents, suspending agent, thickeners, viscosity increasing agents, waxes and mixtures thereof.

Anti-adherents (anti-sticking agents, glidants, flow promoters, lubricants) include, by way of non-limiting example, talc, magnesium stearate, fumed silica (Carbosil, Aerosil), micronized silica (Syloid No FP 244, Grace U.S.A.), polyethylene glycols, surfactants, waxes, stearic acid, stearic acid salts, stearic acid derivatives, starch, hydrogenated vegetable oils, sodium benzoate, sodium acetate, leucine, PEG-4000 and magnesium lauryl sulfate. Antioxidants include, by way of non-limiting example, BHT, BHA, gallic acid, propyl gallate, ascorbic acid, ascorbyl palmitate, 4-hydroxymethyl-2,6-di-tert-butyl phenol, and tocopherol. Binders (adhesives), i.e., agents that impart cohesive properties to powdered materials through particle-particle bonding, include, by way of non-limiting example, matrix binders (dry starch, dry sugars), film binders (PVP, starch paste, celluloses, bentonite, sucrose), and chemical binders (polymeric cellulose derivatives, such as carboxy methyl cellulose, HPC and HPNC, sugar syrups; corn syrup; water soluble polysaccharides such as acacia, tragacanth, guar and alginates; gelatin, gelatin hydrolysate; agar; sucrose; dextrose, and non-cellulosic binders, such as PVP, PEG, vinyl pyrrolidone copolymers, pregelatinized starch, sorbitol, and glucose) Buffering agents, include an acid and a base, wherein the acid is a pharmaceutically acceptable acid, such as hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, and the base is a pharmaceutically acceptable base, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a salt of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid. Chelating agents include, by way of non-limiting example, EDTA and EDTA salts Colorants or opaquants include, by way of non-limiting example, titanium dioxide, food dyes, lakes, natural vegetable colorants, iron oxides, silicates, sulfates, magnesium hydroxide and aluminum hydroxide. Diluents or fillers include, by way of non-limiting example, lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose. Disintegrants and super disintegrants include, by way of non-limiting example, croscarmellose sodium, starch, starch derivatives, clays, gums, cellulose, cellulose derivatives, alginates, crosslinked polyvinypyrrolidone, sodium starch glycolate and microcrystalline cellulose. Flavorants or desensitizers include, by way of non-limiting example, spray-dried flavors, essential oils and ethyl vanillin. Plasticizers include, by way of non-limiting example, polyethylene glycol, citrate esters (e.g., triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl seccate. Preservatives include, by way of non-limiting example, ascorbic acid, boric acid, sorbic acid, benzoic acid, and salts thereof, parabens, phenols, benzyl alcohol, and quaternary ammonium compounds. Solvents include, by way of non-limiting example, alcohols, ketones, esters, chlorinated hydrocarbons and water. Sweeteners include, by way of non-limiting example, natural sweeteners such as maltose, sucrose, glucose, sorbitol, glycerin and dextrins, and artificial sweeteners, such as aspartame, saccharine and saccharine salts. Thickeners (viscosity modifiers, thickening agents, solidifying agents) include, by way of non-limiting example, sugars, polyvinylpyrrolidone, cellulosics, polymers, high molecular weight polyethylene glycols (e.g., PEG 8000), and alginates. Additives also include, by way of non-limiting example, proteins (e.g., collagen, gelatin, Zein, gluten, mussel protein, lipoprotein); carbohydrates (e.g., alginates, carrageenan, cellulose derivatives, pectin, starch, chitosan): gums (e.g., xanthan gum, gum arabic); spermaceti; natural or synthetic waxes; carnuaba wax, fatty acids (e.g, stearic acid, hydroxystearic acid), fatty alcohols; sugars; shellacs, such as those based on sugars (e.g., lactose, sucrose, dextrose) or starches: polysaccharide-based shellacs (e.g., maltodextrin and maltodextrin derivatives, dextrates, cyclodextrin and cyclodextrin derivatives); cellulosic-based shellacs (e.g., microcrystalline cellulose, sodium carboxymethyl cellulose, hydroxypropylmethyl cellulose, ethyl cellulose, hydroxypropyl cellulose, cellulose acetate, cellulose nitrate, cellulose acetate butyrate, cellulose acetate trimellitate, carboxymethylethyl cellulose, hydroxypropylmethyl cellulose phthalate); inorganics, such as dicalcium phosphate, hydroxyapitite, tricalcium phosphate, talc and titania; polyols, such as mannitol, xylitol and sorbitol; polyethylene glycol esters; and polymers, such as alginates, poly (lactide coglycolide), gelatin, crosslinked gelatin, and agar-agar.

In some embodiments, the at least one pharmaceutically acceptable carrier is any carrier suitable for delivering an efficacious amount of a steroidal compound, e.g., a testosterone alkyl ester, to an individual. In some embodiments, the at least one pharmaceutically acceptable carrier is or comprises a hydrophilic carrier (e.g., a hydrophilic surfactant or hydrophilic additive). In certain embodiments, the at least one pharmaceutically acceptable carrier is a lipophilic carrier (e.g., a lipophilic surfactant or lipophilic additive). In some embodiments, the at least one pharmaceutically acceptable carrier is a hydrophilic carrier (e.g., a hydrophilic surfactant or hydrophilic additive) and a lipophilic carrier (e.g., a lipophilic surfactant or lipophilic additive). In certain embodiments, the hydrophilic carrier is a hydrophilic triglyceride. In specific embodiments, the hydrophilic triglyceride is a polyoxylated castor oil, or a polyoxylated hydrogenated castor oil. In some embodiments, any pharmaceutical composition provided herein consists essentially of a lipophilic carrier or combination of lipophilic carriers. In certain embodiments, any pharmaceutical composition provided herein comprises a lipophilic carrier and less than 10% w/w, less than 5% w/w or is substantially free of a hydrophilic carrier. In certain embodiments, any pharmaceutical composition provided herein comprises a lipophilic carrier and less than 10% w/w, less than 5% w/w or is substantially free of a hydrophilic carrier. In some embodiments, the pharmaceutical composition comprising a carrier (e.g., a hydrophilic carrier and/or a lipophilic carrier), the pharmaceutical composition is a solid, a semi-solid, a gel, a jelly, a paste, or the like. In certain embodiments, e.g., wherein a pharmaceutical composition comprising a hydrophilic carrier and/or a lipophilic carrier, a viscosity enhancing agent or a solidifying agent (solidifier) is utilized to afford a pharmaceutical composition that is a solid, a semi-solid, a gel, a jelly, a paste, or the like. Thus, in certain embodiments, the at least one pharmaceutically acceptable carrier is a hydrophilic carrier (e.g., a hydrophilic surfactant or hydrophilic additive) and a viscosity enhancing or solidifying agent (solidifier). In certain embodiments, the at least one pharmaceutically acceptable carrier is a lipophilic carrier (e.g., a lipophilic surfactant or lipophilic additive) and a viscosity enhancing or solidifying agent (solidifier). In some embodiments, the at least one pharmaceutically acceptable carrier is or comprises a hydrophilic carrier (e.g., a hydrophilic surfactant or hydrophilic additive), a lipophilic carrier (e.g., a lipophilic surfactant or lipophilic additive), and a viscosity enhancing or solidifying agent (solidifier). In some embodiments, the at least one pharmaceutically acceptable carrier is or comprises a hydrophilic carrier (e.g., a hydrophilic surfactant or hydrophilic additive), a lipophilic carrier (e.g., a lipophilic surfactant or lipophilic additive), and an antioxidant. In some embodiments, the at least one pharmaceutically acceptable carrier is or comprises a hydrophilic carrier (e.g., a hydrophilic surfactant or hydrophilic additive), a lipophilic carrier (e.g., a lipophilic surfactant or lipophilic additive), a viscosity enhancing or solidifying agent (solidifier), and an antioxidant. In some embodiments, the at least one pharmaceutically acceptable carrier is or comprises an amphiphilic or zwitterionic carrier (e.g., an ampiphilic surfactant or ampiphilic additive). In certain embodiments, the pharmaceutically acceptable carrier is any carrier suitable for achieving one or more of the pharmacokinetic and/or pharmacodynamic profiles set forth herein.

Solidifying agents (solidifier) include, by way of non-limiting example, PEG 3350, PEG 4000, PEG 6000, PEG 8000, Poloxamer 188, Poloxamer 407, cetyl esters, wax, beeswax, glyceryl palmitostearate, stearic acid, and so on.

Referring to FIG. 1, absolute actual PK levels were obtained with a single dose TD administration from a composition comprising a lipophilic and a hydrophilic additive.

Referring to FIG. 1, disclosed are simulated absolute value changes with a daily dose of 600 mg (however, the lowest daily dose can be a slow as 200 mg/day), to support some of the threshold values in the embodiments: change in T $C_{avg}$, FreeT increase, SHBG lowering, Albumin increase, HBlac decrease, Ammonia decrease, muscle mass increase, fat mass decrease, and TNF decrease.

TDPC Compositions of the instant invention were prepared and assessed for its performance characteristics such as physical form for fully solubilized with no TD crystal upon preparation and upon storage. A solubilized form of TD in a single unit dosage form is convenient and preferred for biopharmaceutical performance as well as stability during storage imparting adequate shelf life. It was surprisingly found that compositions: F3, F4, F8, F9, F12, and F14 as described in Table F resulted in solubilized TD with no apparent suspended undissolved crystal with loading of at least 25% w/w that can be formulated as a single unit stable dosage form. Moreover, a lipohilic additive to hydrophilic surfactant ratio of at least 7, and fatty acid to hydrophilic surfactant is at least 6. It was also surprisingly found that TD compositions with TD/Fatty acid ratio of at least four but no more than 2 was critical to enable a solubilized composition that can be encapsulated into a single unit dosage form enabling smaller and singular dosage form for convenient dosing and performance no undissolved drug crystal upon manufacture of storage.

In contrast, compositions F1, F2, F5, F6, F7, F10, F11 and F13 as described in Table F had undissolved crystalline form of TD in the composition when formulated a single unit dosage form at the desired drug loading of at least 25% w/w and moreover had unfavorable characteristics of a suspension with undissolved TD crystals potentially leading to compromised dissolution/absorption performance, and upon RT storage demonstrated undesirable physical attributes with TD undissolved TD crystals.

Exemplary markers of the instant invention (preferably relative to a comparable non-TD administration) may include, for example, at least about 1 unit (SBP, 1 mmHg), less HDL lowering reverse or less lowering, a mean reduction in HDL by at least about 1 mg/dL. Exemplary benefits of the instant invention may include, for example, higher bacterial inhibition activity relative other fatty acid esters (e.g., with regard to *E. coli* inhibition), or an inhibition activity benefit that is 2 times greater relative to TU (at least 50% better than a TU administration).

Through the oral pharmaceutical compositions or dosage forms exemplified in the present invention, modulation to the composition or form of comprised TD may allow for a predetermined increase in antibacterial benefit. Treatment using a TDPC may enable an increase or lack of decrease in antibacterial benefit, an increase or lack of decrease in antifungal benefit, an increase or lack of decrease in antiviral benefit, or any combination thereof. As used herein, descriptions of the present invention when describing antibacterial benefit also apply to the potential of antifungal benefit or antiviral benefit. By way of example, a subject expected to have a decrease in antibacterial activity may see a lower decrease, no change, or an increase in antibacterial activity. By way of another example, a subject may see an increase in antibacterial activity.

By way of non-limiting example, treatment using a TDPC may inhibit bacterial activity that may include, *Propionibacterium acnes, Staphylococcus aureus,* Meticillin-Sensitive *Staphylococcus Aureus,* Methicillin-tesistant *Staphylococcus aureus, Staphylococcus epidermis, Eschericia coli* (Migula) Castellani and Chalmers 25922 (ATCC 25922), Group A Streptococci, Group B Streptococci, Group D Streptococci, *Mycobacterium tuberculosis, Streptococcus pneumonia, Listeria* monocytogeneses, Helycobacter *pylori, Bacteroides* and *Clostridium, Clostridium perfringens,* CNCTC 5459 (*Clostridium perfringens* strain), *Enterococcus faecalis, Clostridium difficile, Proteus mirabilis,* or any combination thereof.

By way of non-limiting example, treatment using a TDPC may inhibit fungal activity that may include, *Candida albicans, Aspergillus niger, fusarium* spp, or any combination thereof.

By way of non-limiting example, treatment using a TDPC may inhibit viral activity that may include, Vesicular stomatitis virus, Herpes simplex virus, Herpes simplex virus type 1, Herpes simplex virus type 2, Visna virus, Respiratory syncytial virus, Junin virus, or any combination thereof.

The formulation and manufacturing of a TDPC may affect antibacterial benefit. By way of example, a formulation of a TDPC that has a hydrophilic carrier (e.g., hydrogenated polyoxyl vegetable oil or glyceride, PEG glyceride of fatty acid ester, polyglycerol-10 fatty acid ester, polysorbate 20, poloxamer, polysorbate 80, polyoxyl 40 hydrogenated castor oil, Polyoxyl 35 castor oil, sodium lauryl sulfate, sodium docusate, poloxamer, polyethylene glycol 1000 tocopherol succinate, PEG) may have higher antibacterial benefit than a TDPC that does not have a hydrophilic carrier. Similarly, a TDPC that has less than about 40%, 30%, 20%, 10%, or 5% w/w % hydrophilic carrier may have higher antibacterial benefit than a TDPC that has a greater hydrophilic carrier. By way of another example, a formulation of a TDPC that has a lipophilic carrier (e.g., a lipophilic surfactant or lipophilic additive) may have higher antibacterial benefit than a TDPC that does not have a lipophilic carrier. Similarly, a TDPC that has greater than about 10%, 20%, 30%, 40%, 50%, or 60% w/w % lipophilic carrier may have higher antibacterial benefit than a TDPC that has a lower w/w % lipophilic carrier.

By way of another example, the formulation and manufacturing of a TDPC, having an effective amount of TD, may have higher antibacterial benefit than a testosterone undecanoate pharmaceutical composition (TUPC) having an effective amount for administration of testosterone undecanoate (TU). Therefore, a non-undecanoate testosterone ester pharmaceutical composition may have a higher antibacterial benefit when compared to a TUPC.

By way of another example, antibacterial benefit may occur when enough loading of a non-undecanoate testosterone ester is present, and the ester provides antibacterial benefit. For example, when the formation of Enterhemorrhagic *E. Coli* (EHEC) biofilms is compared between EHEC formed in the presence of undecanoic acid, and EHEC formed in the presence of lauric acid, lauric acid repressed EHEC biofilms significantly differently than the control (p<0.001) while undecanoic acid did not. Furthermore, lauric acid has been reported to have a antibacterial benefit for *Propionibacterium acnes, Staphylococcus aureus,* Meticillin-Sensitive *Staphylococcus Aureus,* Methicillin-tesistant *Staphylococcus aureus, Staphylococcus epidermis, Eschericia coli* (Migula) Castellani and Chalmers 25922 (ATCC 25922), Group A Streptococci, Group B Streptococci, Group D Streptococci, *Mycobacterium tuberculosis, Streptococcus pneumonia, Listeria* monocytogeneses, Helycobacter *pylori, Bacteroides* and *Clostridium, Clostridium perfringens,* CNCTC 5459 (*Clostridium perfringens* strain), *Enterococcus faecalis, Clostridium difficile,* and *Proteus mirabilis,* antifungal benefit for *Candida albicans, Aspergillus niger,* and *Fusarium* spp, and antiviral benefit for Vesicular stomatitis virus, Herpes simplex virus, Herpes simplex virus type 1, Herpes simplex virus type 2, Visna virus, Respiratory syncytial virus, and Junin virus. The formulation and manufacture of a TDPC may allow for a biorelevant amount of lauric acid administration that may enhance antibacterial benefit. By way of example, cleaving of the laurate ester of TD in the formation of biologically active testosterone may provide an amount of lauric acid that would allow for antibacterial benefit.

Exemplary oral composition single dose was administered once a day with serum drug blood levels monitored over a 24 week period at day 1, week 4, week 8, week 12, week 16, week 20, and week 24. CT scans of the L3 region were also collected at screening, week 12, and week 24. Exemplary oral composition was administered in a double-blind trial to subjects with sarcopenia and cirrhosis that were awaiting a liver transplant, randomized to receive exemplary oral composition (LPCN 1148 (i.e. TDPC)), or a placebo for 24 weeks.

Topline results following the 24 week treatment period show a change from baseline of L3-SMI of 4.4 cm$^2$/m$^2$ in LPCN 1148 subjects when compared to placebo with a 95% CI of 1.3 cm$^2$/m$^2$ to 7.4 cm$^2$/m$^2$. Topline results following the 12 week treatment period show a change from baseline for L3-SMI of 2.6 cm$^2$/m$^2$ in LPCN 1148 subjects with a 95% CI of 0.8 cm$^2$/m$^2$ to 4.5 cm$^2$/m$^2$. Additionally, topline results following the 24 week treatment period show a change from baseline for L3-SMI of 3.6 cm$^2$/m$^2$ in LPCN 1148 subjects with a 95% CI of 1.7 cm$^2$/m$^2$ to 5.5 cm$^2$/m$^2$.

Figure 2:
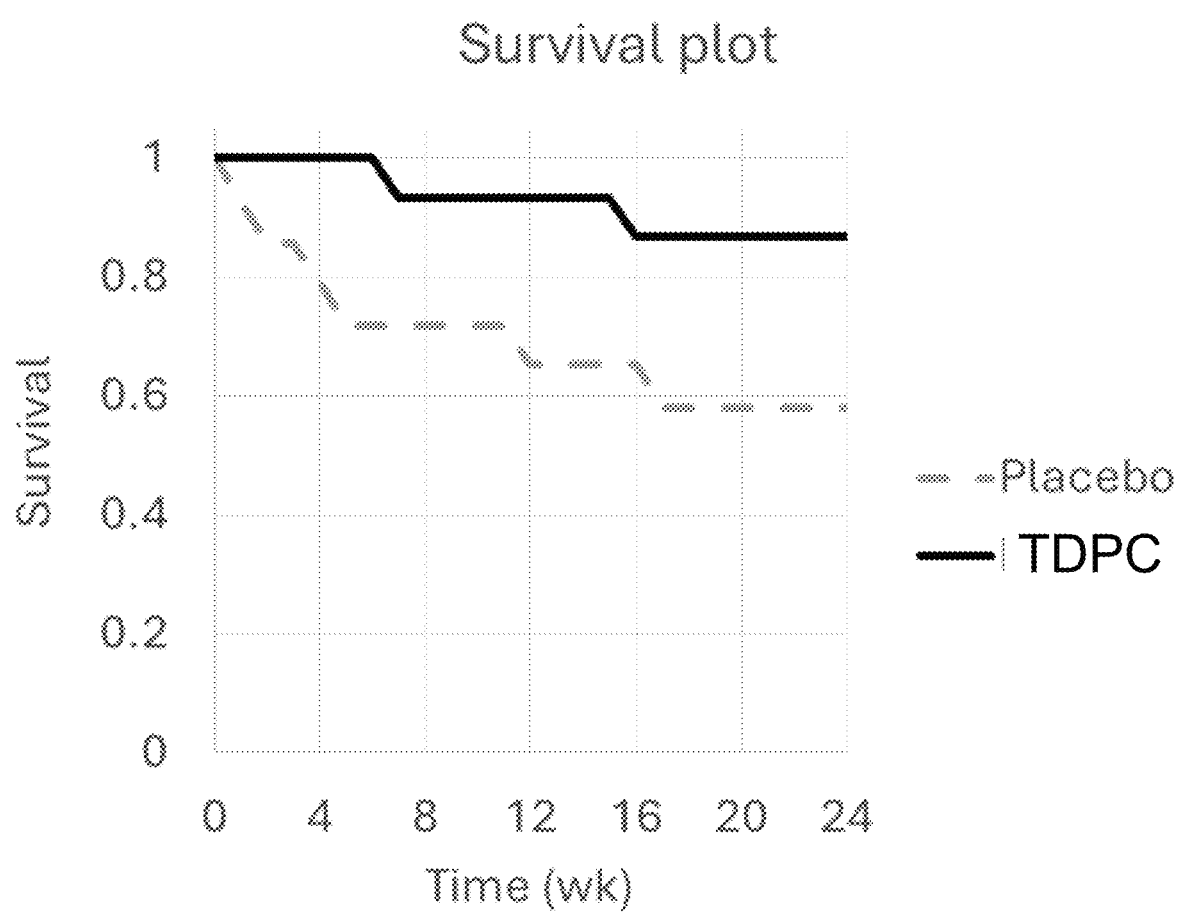
FIG. 2 is a survival plot of a comparison between an exemplary administration of TD and administration of a placebo.

Topline results following the 24 week treatment period show 2 HE events with CTAE grade greater than 1 in LPCN 1148 when compared to 6 HE events with CTAE grade greater than 1 in placebo. In a similar manner, the survival estimate of HE events is shown in FIG. 2, which presents a lower probability of HE events over time may occur during the administration of LPCN 1148 when compared to the placebo administration. The risk outcome may similarly be characterized by the hazard ratio for HE events, which shows the subject risk over time between LPCN 1148 and placebo treatment. A hazard ratio (e.g., LPCN 1148 divided by placebo) of less than one describes a lower hazard or probability of an event occurring. The hazard ratio when comparing LPCN 1148 to placebo is calculated to be 0.266 with a standard error of 0.298. This hazard ratio considers HE events and the amount of time each HE event is present during the 24 week trial, the total number of subjects decreases with each HE event occurrence, and increases once the HE event has ended.

Topline results following the 24 week treatment period shows and increase in hemoglobin of 1.30 g/dL in LPCN 1148 when compared to change of −0.16 g/dL in placebo, this change was statistically significant for LPCN 1148 when compared to 0 and when compared to placebo. The topline results following the 24 week treatment period additionally showed a decrease in the overall number of anemia status subjects from 11 subject in LPCN 1148 (73%) at baseline to 7 subjects (47%) at week 24 accounting for a resolution of anemia in 4 subjects (36%) and no subjects with new onset anemia status (0%). There was no change in the number of anemia status subjects from 7 subjects in placebo (50%) at baseline to 7 subjects (54%) at week 24 accounting for a resolution of anemia in 1 subject (14%) and 1 subject (17%) with new onset anemia status. Treatment using LPCN 1148 may allow for an increase in resolution of anemia status.

TABLE H1

Mean PGI-C in LPCN 1148 and placebo at visit periods

| | LPCN 1148 | | Placebo | |
|---|---|---|---|---|
| Visit | n | PGI-C | n | PGI-C |
| Week 4 | 13 | 2.62 | 13 | 3.69 |
| Week 8 | 13 | 3.00 | 13 | 3.85 |
| Week 12 | 15 | 3.20 | 13 | 3.54 |
| Week 16 | 15 | 2.53 | 13 | 3.92 |
| Week 20 | 15 | 3.00 | 13 | 3.46 |
| Week 24 | 15 | 3.00 | 13 | 3.85 |

Topline results are presented in Table H1. Topline results following 4 week treatment period show a mean PGI-C score of 2.62 in LPCN 1148 subjects and 3.69 in placebo subjects. Topline results following 8 week treatment period show a mean PGI-C score of 3.00 in LPCN 1148 subjects and 3.85 in placebo subjects. Topline results following 12 week treatment period show a mean PGI-C score of 2.6 in LPCN 1148 subjects and 3.69 in placebo subjects. Topline results following 16 week treatment period show a mean PGI-C score of 2.53 in LPCN 1148 subjects and 3.92 in placebo subjects. Topline results following 20 week treatment period show a mean PGI-C score of 3.00 in LPCN 1148 subjects and 3.46 in placebo subjects. Topline results following 24 week treatment period show a mean PGI-C score of 3.00 in LPCN 1148 subjects and 3.85 in placebo subjects.

Topline results following the 24 week treatment period show a change from baseline of IMAT area of −1.25 cm$^2$ in LPCN 1148 subjects when compared to placebo. Similarly, topline results following the 24 week treatment period show a change from baseline for HQM area of 10.82 cm$^2$ in LPCN 1148 subjects when compared to placebo. Additionally, topline results following the 24 week treatment period show a change from baseline for LQM area of 3.91 cm$^2$ in LPCN 1148 subjects when compared to placebo.

Topline results following the 24 week treatment period show a change in a 6 minute walk test of 270 feet in LPCN 1148 when compared to −16 feet in placebo. Additionally, the change in the total time to complete the EncephalApp Stroop Test showed −4.8 seconds in LPCN 1148, while 13.8 seconds in placebo. Additionally, the total number of days in hospitalization in LPCN 1148 was 54 days, while 117 days in placebo. Treatment using LPCN 1148 may provide a benefit in 6 minute walk test, or Stroop Test.

Through the oral pharmaceutical compositions or dosage forms exemplified in the present invention, modulation to the composition or form of comprised TD may allow for a predetermined increase in muscle mass or a predetermined lack of a decrease in muscle mass. Treatment using a TDPC may enable an increase or lack of a decrease in L3-SMI. By way of example a subject expected to lose muscle mass (e.g., a subject with an end stage liver disease) may experience an increase or lack of a decrease in L3-SMI. Treatment using a TDPC may enable a subject to experience fewer decompensation events (e.g., HE). Treatment using a TDPC may reduce the risk of overt HE recurrence. Treatment using a TDPC may enable a subject experiencing a decompensation event (e.g., HE) while on treatment to experience a faster recovery from the decompensation event. Treatment using a TDPC may enable a subject's impression of their quality of life increasing (e.g., PGI-C). Treatment using a TDPC may enable an increase in a subject's muscle quality (e.g., decrease in IMAT, increase in low quality muscle (LQM), increase in high quality muscle (HQM)).

Exemplary benefits from the topline results suggest that an overall benefit may occur at a time that includes 4 weeks, 8 weeks, 12 weeks, 16 weeks, 20 weeks, and 24 weeks following start of treatment. By way of example, a benefit may occur as early as 4 weeks. By way of another example, a benefit may occur as early as 12 weeks. By way of another example, a benefit may occur as early as 24 weeks.

The benefits of maintaining or improving muscle in a population that has decreased muscle mass and quality over time may be applied to concomitant treatment with a treatment where muscle loss may be a side effect or muscle gain may enhance treatment. For example, GLP-1 agonist treatments have been known to lower overall body weight loss, however as much as 40% of that weight loss might come from lean mass loss (see for instance the article entitled "Once-Weekly Semaglutide in Adults with Overweight or Obesity" which was published on Feb. 10, 2021 in Vol. 384 No. 11 of the New England Journal of Medicine (NEJM) and which can be found on website of the NEJM such as at: https://www.nejm.org/doi/full/10.1056/NEJMoa2032183). By way of example, an oral pharmaceutical composition similar to the oral pharmaceutical composition used in LPCN 1148 treatment may be used concomitantly with a GLP-1 agonist treatment. GLP-1 agonist may be selected from pemvidutide, semaglutide, liraglutide, dulaglutide, tirzepatide, native GLP-1, dulaglutide, exenatide, exenatide ER, lixisenatide, albiglutide, or other GLP-1 agonist peptides. Concomitant treatment that includes an oral pharmaceutical composition that comprises or is prepared from TD (TDPC) may decrease the percentage of weight loss that is lean mass during muscle loss. Concomitant treatment that includes TDPC may keep or increase lean mass during muscle loss.

By way of example, the percentage of weight loss that is lean mass during weight loss due to concomitant or follow up treatment that includes TDPC may include 30%, 20%, 15%, 10%, 5%, 0%, −5%, and −10% (negative % loss representing % muscle gained during weight loss). By way of example, the percentage of weight loss that is lean mass during weight loss due to concomitant or follow up treatment may be 5%. By way of another example, the percentage of weight loss that is lean mass during weight loss due to concomitant or follow up treatment may be 0%. By way of yet another example, the percentage of weight gain that is lean mass during weight loss due to concomitant or follow up treatment may be 5%.

What is claimed is:

1. A method of treating a condition in a subject, said method comprising orally administering a pharmaceutical substance to said subject, wherein said pharmaceutical substance comprises or is prepared from a TDPC and wherein in comparison to at least one of a TDPC pre-administration state of said subject and a placebo administration, said administration results in at least one of:
   no deterioration in said subject of at least one of cardiovascular risk, cardiovascular health, prostate health, muscle health, CNS health, GI health, cell health, and median hospitalization duration, and
   an improvement in said subject of at least one of cardiovascular risk, cardiovascular health, prostate health, muscle health, CNS health, GI health, cell health, and median hospitalization duration.

2. The method of claim 1, wherein said administration results in said subject in at least one of:
   a decrease in an SHBG (sex hormone binding globulin) level,
   an increase in an albumin level,
   a decrease in frailty,
   a decrease in sarcopenia,
   a decrease in myosteatosis,
   a decrease in fat mass,
   a decrease in systemic ammonia,
   a decrease in portal hypertension,
   a decrease in an abnormally high level of at least one of ALT, AST, GGT, and ALP,
   an increase in lean mass,
   an increase in free Testosterone,
   an increase in total Testosterone $C_{avg}$ by at least 100 ng/dl,
   an increase in a hematocrit level,
   an increase in a hemoglobin level,
   a decrease in inflammation markers,
   an increase in L3-SMI (Skeletal Muscle Index),
   a decrease in PGI-C,
   a decrease in HE events,
   a decrease in VAT (Visceral Adipose Tissue),
   a decrease in SAT (Subcutaneous Adipose Tissue),
   a decrease in FAT (VAT plus SAT),
   an increase in muscle area, and
   a decrease in IMAT.

3. The method of claim 1, wherein said administering results in concurrent improvement in muscle heath and CNS health.

4. The method of claim 1, wherein said subject has liver cirrhosis and at least one of:
   a MELD score of at least 12,
   a MELD score of no more than 25,
   a MELD score in the range of 12 to 25,
   at least one decompensation event,
   a BMI >20,
   an L3 muscle skeletal Index of <55 cm2/m2,
   a liver frailty index of >3,
   an ALT/AST ratio of about 1,
   an AST of >40 U/L,
   an abnormal ALT level, and
   an abnormal ALP level.

5. The method of claim 4, wherein a total daily dose of said pharmaceutical substance comprises an amount of about 150 mg to about 600 mg administered in a regimen of at least one of once a day and twice a day.

6. The method of claim 1, wherein said subject has liver cirrhosis and a plurality of:
   a MELD score of at least 12,
   a MELD score of no more than 25,
   a MELD score in the range of 12 to 25,
   at least one decompensation event,
   a BMI >20,
   an L3 muscle skeletal Index of <55 cm2/m2,
   a liver frailty index of >3,
   an ALT/AST ratio of about 1,
   an AST of >40 U/L,
   an abnormal ALT level, and
   an abnormal ALP level.

7. The method of claim 1, wherein said subject has at least one of dysregulated proteostatis, an abnormally high SHBG level, and an abnormally low albumin level, and
   wherein said subject is in need of testosterone intervention based on a morning baseline testosterone level of at least one of <400 ng/dl, <350 ng/dL, <300 ng/dL, and <250 ng/dL.

8. The method of claim 1, wherein said cardiovascular risk comprises risk of an adverse change in at least one of SBP, DBP, an HDL level, occurrence of ascites, a homocysteine level, and cardiac muscle mass or strength, and
   wherein said deterioration of cardiovascular health comprises an adverse change in at least one of SBP, DBP, an HDL, occurrence of ascites, a homocysteine level, a cardiac reactive protein level, and cardiac muscle mass or strength, and
   wherein said improvement of cardiovascular health comprises a favorable change in at least one of SBP, DBP, an HDL level, a homocysteine level, and cardiac muscle mass or strength, and
   wherein said deterioration of prostate health comprises an adverse change in at least one of prostate gland size, prostate gland weight, and a BPH symptom, and
   wherein said improvement of prostate health comprises a favorable change in at least one of prostate gland size, prostate gland weight, and a BPH symptom, and wherein said deterioration of muscle health comprises an adverse change in at least one of muscle mass, muscle strength, muscle function, and muscle toxicity, and wherein said improvement of muscle health comprises a favorable change in at least one of muscle mass, muscle strength, muscle function, and muscle toxicity, and wherein said deterioration of CNS or GI health comprises an adverse change in at least one of depression, seizure occurrence, cognition, risk of HE occurrence, risk of recurrence of overt HE of a grade of greater than 1.0, HE recurrence, breakthrough HE episodes, HE related hospitalizations, a length of time between HE hospitalizations, fewer subjects having HE events or HE grade greater than 1.0 events by at least one of at least at least about 20%, at least about 30%, at least about 40%, at least about 50%, at least about 60%, at least about 70%, and at least about 80%, fewer HE events by at least one of at least at least about 20%, at least about 30%, at least about 40%, at least about 50%, at least about 60%, at least about 70%, and at least about 80%, fewer HE grade 1.0 or greater events by at least one of at least at least about 20%, at least about 30%, at least about 40%, at least about 50%, at least about 60%, at least about 70%, and at least about 80%, fewer overt HE events by at least one of at least at least about 20%, at least about 30%, at least about 40%, at least about 50%, at least about 60%, at least about 70%, and at least about 80%, duration of time to onset of an episode of overt HE, HE recurrence reversal, occurrence of asterixis, mental status, intellectual function, psychometric test results, and neurophysiologic test results, and wherein said improvement of CNS health comprises a favorable change in at least one of depression, seizure occurrence, cognition, risk of HE occurrence, risk of recurrence of overt HE of a grade of greater than 1.0, HE recurrence, breakthrough HE episodes, HE related hospitalizations, a length of time between HE hospitalizations, fewer subjects having HE events or HE grade greater than 1.0 events by at least one of at least at least about 20%, at least about 30%, at least about 40%, at least about 50%, at least about 60%, at least about 70%, and at least about 80%, fewer HE events by at least one of at least at least about 20%, at least about 30%, at least about 40%, at least about 50%, at least about 60%, at least about 70%, and at least about 80%, fewer HE grade 1.0 or greater events by at least one of at least at least about 20%, at least about 30%, at least about 40%, at least about 50%, at least about 60%, at least about 70%, and at least about 80%, fewer overt HE events by at least one of at least at least about 20%, at least about 30%, at least about 40%, at least about 50%, at least about 60%, at least about 70%, and at least about 80%, duration of time to onset of an episode of overt HE, HE recurrence reversal, occurrence of asterixis, mental status, intellectual function, psychometric test results, and neurophysiologic test results, and wherein said deterioration of GI health comprises an adverse change in at least one of diarrhea, microbial infection, *Clostridium difficile* infection, advanced liver disease, chronic liver disease, liver cirrhosis, chronic liver failure, quantity of liver injury markers, end-stage liver disease, hepatic fibrosis, hepatic inflammation, hepatic steatosis, NASH, NAFLD, pre-liver transplant condition, post-liver transplant condition, PSC, and PBC, and wherein said improvement of GI health comprises a favorable change in at least one of diarrhea, microbial infection, *Clostridium difficile* infection, advanced liver disease, chronic liver disease, liver cirrhosis, chronic liver failure, quantity of liver injury markers, end-stage liver disease, hepatic fibrosis, hepatic inflammation, hepatic steatosis, NASH, NAFLD, pre-liver transplant condition, post-liver transplant condition, PSC, and PBC.

9. The method of claim 8, wherein said adverse change in SBP comprises an increase of SBP of at least 1.7 mmHg, and wherein said favorable change in SBP comprises a decrease of SBP of at least 1 mmHg.

10. The method of claim 1, wherein said condition comprises at least one of carcinoma, sarcoma, melanoma, lymphoma, leukemia, end-stage liver disease, advanced liver disease, chronic liver disease, end-stage lung disease, chronic kidney disease, end-stage kidney disease, end-stage musculoskeletal system disease, end-stage cardiovascular disease, end-stage blood disease, end-stage endocrine gland disease, end-stage gastrointestinal disease, end-stage skin disease, end-stage genital organ disease, end-stage central nervous system disease, hepatic fibrosis, hepatic inflammation, hepatic steatosis, HE, recurrence of overt HE, NASH, NAFLD, pre/post liver transplant, decompensated cirrhosis, PBC, PSC, ILD, pneumonia, IPF, muscle mass wasting, cachexia, sarcopenia, frailty, type 1 diabetes, type 2 diabetes, hyperglycemia, glucose intolerance, hypogonadism, hypogonadotropic hypogonadism, a metabolic syndrome, visceral adiposity, obesity, impaired wound healing, large waist, myosteatosis, cancer, CHF, pulmonary fibrosis, COPD, and hereditary angioedema.

11. The method of claim 1, wherein said pharmaceutical substance further comprises at least one additive.

12. The method of claim 11, wherein said at least one additive further comprises at least one of a lipophilic additive and a hydrophilic additive.

13. The method of claim 1, wherein said TDPC comprises at least one of:
TD comprising by wt % of said TDPC about 27 to about 32,
a hydrophilic surfactant comprising no more than about 5 wt % of said TDPC, and
an excipient comprising by wt % of said TDPC at least one of a minimum of 50, a minimum of 55, a minimum of 60, a minimum of 65, and a minimum of 70.

14. The method of claim 1, wherein said pharmaceutical composition substance further comprises at least one carrier.

15. The method of claim 14, wherein said at least one carrier, further comprises at least one of a lipophilic carrier and a hydrophilic carrier.

16. The method of claim 15, wherein said at least one lipophilic carrier further comprises at least one of a lipophilic surfactant and a lipophilic additive, and wherein said hydrophilic carrier further comprises at least one of a hydrophilic surfactant and a hydrophilic additive.

17. The method of claim 15, wherein said at least one lipophilic carrier comprises at least one of a fatty acid, a derivative of a fatty acid, a vegetable oil, a derivative of a vegetable oil, a monoglyceride, a diglyceride, a triglyceride, a derivative of a monoglyceride, a derivative of a diglyceride, a derivative of a triglyceride, a sterol, a phytosterol, a tocopherol, a tocotrienol, or its derivative, a tocopherol succinate, a tocopherol acetate and a fish oil, and wherein said hydrophilic carrier comprises at least one of a polyoxyethylene hydrogenated vegetable oil, a polyoxyethylene vegetable oil, a polyethylene glycol fatty acid ester, a polyethylene glycol fatty acid monoglyceride mixture, a polyethylene glycol fatty acid diglyceride mixture, a polysorbate, a polyethylene glycol derivative of tocopherol, an alcohol, and an alcohol derivative.

18. The method of claim 17, wherein said at least one fatty acid comprises at least one of an oleic acid, a lauric acid, a stearic acid, and a derivative thereof, and wherein said vegetable oil comprises at least one of a peppermint oil, a sesame oil, a borage oil, a castor oil, a maize oil, a cottonseed oil, and a derivative thereof, and wherein said derivative of monoglyceride comprises at least one of glyceryl monolinoleate, and sorbitan mono-fatty acid, and wherein said derivative of diglyceride comprises glyceryl palmitostearate, and wherein said polyoxyethylene hydrogenated vegetable oil comprises PEG hydrogenated castor oil, and wherein said alcohol comprises at least one of ethyl alcohol and benzyl alcohol, and wherein said alcohol derivative comprises benzyl benzoate.

19. The method of claim 1, wherein said pharmaceutical substance further comprises at least one of a tablet, a capsule, a caplet, a gelcap, a suspension, a solution, a drink, a gel, a syrup, a dispersion, an emulsion, a sprinkle, a lozenge, a microemulsion, a nanoemulsion, an elixir, a paste, a powder, and a granule.

20. The method of claim 1, wherein said method comprises at least one of:
a dosing regimen comprising at least one of a QD regimen and a BID regimen,
a dosing regimen comprising at least one of a titration regimen and a non-titration regimen,
administration of a total daily dose of TD of at least one of about 150 mg to about 1,000 mg, about 350 mg to about 850 mg, and about 500 mg to about 700 mg, and
said TDPC having a dosage form comprising a single unit dosage form, a two unit dosage form, a three unit dosage for, and a four unit dosage form.

21. The method of claim 1, wherein said TDPC comprises or is prepared from at least one lipophilic additive, said at least one lipophilic additive comprising at least one of a fatty acid, a fatty acid derivative, and a combination thereof.

22. The method of claim 21, wherein said administration results in said subject in at least one of:
a decrease in an SHBG level,
an increase in an albumin level,
a decrease in frailty,
a decrease in sarcopenia,
a decrease in myosteatosis,
a decrease in fat mass,
a decrease in systemic ammonia,
a decrease in portal hypertension,
a decrease in an abnormally high level of at least one of ALT, AST, GGT, and ALP,
an increase in lean mass,
an increase in free T,
an increase in total T $C_{avg}$ by at least 100 ng/dL,
an increase in a hematocrit level,
an increase in a hemoglobin level,
a decrease in inflammation markers,
an increase in L3-SMI,
a decrease in PGI-C,
a decrease in HE events,
a decrease in VAT,
a decrease in SAT,
a decrease in FAT,
an increase in muscle area, and
a decrease in IMAT.

23. The method of claim 21, wherein said fatty acid comprises at least one of an oleic acid or a derivative thereof, a lauric acid or a derivative thereof, a stearic acid or a derivative thereof, and a combination thereof.

24. The method of claim 21, wherein said TDPC comprises w/w ratio of at least one of said TD to said lipophilic additive of at least one of a minimum of about 0.38, about 0.52, and about 0.60, and said TD to a hydrophilic additive of at least one of a minimum of about 4.0, about 5.4, and about 6.5.

25. The method of claim 21, wherein said administering results in concurrent improvement in muscle heath and CNS health.

26. The method of claim 21, wherein said subject has liver cirrhosis with a MELD score of at least 12, and at least one of:
at least one decompensation event,
a BMI >20,
an L3 muscle skeletal Index of <55 cm2/m2,
a liver frailty index of >3,
an ALT/AST ratio of about 1,
an AST of >40 U/L,
an abnormal ALT level, and
an abnormal ALP level.

27. The method of claim 26, wherein a total daily dose of said pharmaceutical substance comprises an amount of about 150 mg to about 600 mg administered in a regimen of at least one of once a day and twice a day.

28. The method of claim 21, wherein said subject has at least one of dysregulated proteostatis, an abnormally high SHBG level, and an abnormally low albumin level, and
wherein said subject is in need of testosterone intervention based on a morning baseline testosterone level of at least one of <400 ng/dL, <350 ng/dL, <300 ng/dL, and <250 ng/dL.

29. The method of claim 21, wherein said cardiovascular risk comprises risk of an adverse change in at least one of SBP, DBP, an HDL level, a homocysteine level, and cardiac muscle mass or strength, and
wherein said deterioration of cardiovascular health comprises an adverse change in at least one of SBP, DBP, an HDL, a homocysteine level, a cardiac reactive protein level, and cardiac muscle mass or strength, and
wherein said improvement of cardiovascular health comprises a favorable change in at least one of SBP, DBP, an HDL level, a homocysteine level, and cardiac muscle mass or strength, and
wherein said deterioration of prostate health comprises an adverse change in at least one of prostate gland size, prostate gland weight, and a BPH symptom, and
wherein said improvement of prostate health comprises a favorable change in at least one of prostate gland size, prostate gland weight, and a BPH symptom, and
wherein said deterioration of muscle health comprises an adverse change in at least one of muscle mass, muscle strength, muscle function, and muscle toxicity, and
wherein said improvement of muscle health comprises a favorable change in at least one of muscle mass, muscle strength, muscle function, and muscle toxicity, and
wherein said deterioration of CNS health comprises an adverse change in at least one of depression, seizure occurrence, cognition, risk of HE occurrence, risk of recurrence of overt HE of a grade of greater than 1.0, HE recurrence, breakthrough HE episodes, HE related hospitalizations, a length of time between HE hospitalizations, fewer subjects having HE events or HE grade greater than 1.0 events by at least one of at least at least about 20%, at least about 30%, at least about 40%, at least about 50%, at least about 60%, at least about 70%, and at least about 80%, fewer HE events by at least one of at least at least about 20%, at least about 30%, at least about 40%, at least about 50%, at least about 60%, at least about 70%, and at least about 80%, fewer HE grade 1.0 or greater events by at least one of at least at least about 20%, at least about 30%, at least about 40%, at least about 50%, at least about 60%, at least about 70%, and at least about 80%, fewer overt HE events by at least one of at least at least about 20%, at least about 30%, at least about 40%, at least about 50%, at least about 60%, at least about 70%, and at least about 80%, duration of time to onset of an episode of overt HE, HE recurrence reversal, occurrence of asterixis, mental status, intellectual function, psychometric test results, and neurophysiologic test results, and wherein said improvement of CNS health comprises a favorable change in at least one of depression, seizure occurrence, cognition, risk of HE occurrence, risk of recurrence of overt HE of a grade of greater than 1.0, HE recurrence, breakthrough HE episodes, HE related hospitalizations, a length of time between HE hospitalizations, fewer subjects having HE events or HE grade greater than 1.0 events by at least one of at least at least about 20%, at least about 30%, at least about 40%, at least about 50%, at least about 60%, at least about 70%, and at least about 80%, fewer HE events by at least one of at least at least about 20%, at least about 30%, at least about 40%, at least about 50%, at least about 60%, at least about 70%, and at least about 80%, fewer HE grade 1.0 or greater events by at least one of at least at least about 20%, at least about 30%, at least about 40%, at least about 50%, at least about 60%, at least about 70%, and at least about 80%, fewer overt HE events by at least one of at least at least about 20%, at least about 30%, at least about 40%, at least about 50%, at least about 60%, at least about 70%, and at least about 80%, duration of time to onset of an episode of overt HE, HE recurrence reversal, occurrence of asterixis, mental status, intellectual function, psychometric test results, and neurophysiologic test results, and wherein said deterioration of GI health comprises an adverse change in at least one of diarrhea, microbial infection, *Clostridium difficile* infection, advanced liver disease, chronic liver disease, liver cirrhosis, chronic liver failure, quantity of liver injury markers, end-stage liver disease, hepatic fibrosis, hepatic inflammation, hepatic steatosis, NASH, NAFLD, pre-liver transplant condition, post-liver transplant condition, PSC, and PBC, and wherein said improvement of GI health comprises a favorable change in at least one of diarrhea, microbial infection, *Clostridium difficile* infection, advanced liver disease, chronic liver disease, liver cirrhosis, chronic liver failure, quantity of liver injury markers, end-stage liver disease, hepatic fibrosis, hepatic inflammation, hepatic steatosis, NASH, NAFLD, pre-liver transplant condition, post-liver transplant condition, PSC, and PBC.

30. The method of claim 1, wherein said TDPC comprises or is prepared from at least one lipophilic additive, said at least one lipophilic additive comprising at least one of a fatty acid, a fatty acid derivative, and a combination thereof, and wherein in comparison to a substantially comparable administration of a pharmaceutical substance comprising TU and being substantially TD-free (NDPC) said administration results in at least one of:

less deterioration in said subject of at least one of a cardiovascular risk, cardiovascular health, prostate health, muscle health, CNS health, GI health, cell health, and median hospitalization duration, and greater improvement in said subject of at least one of a cardiovascular risk, cardiovascular health, prostate health, muscle health, CNS health, GI health, cell health, and median hospitalization duration.

* * * * *